(12) United States Patent
Zhang et al.

(10) Patent No.: US 7,977,064 B2
(45) Date of Patent: Jul. 12, 2011

(54) DISHEVELED PDZ MODULATORS

(75) Inventors: Yingnan Zhang, South San Francisco, CA (US); Mike Costa, San Francisco, CA (US); Sachdev S. Sidhu, Toronto (CA)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/696,875

(22) Filed: Jan. 29, 2010

(65) Prior Publication Data

US 2010/0136580 A1    Jun. 3, 2010

Related U.S. Application Data

(63) Continuation of application No. 11/733,146, filed on Apr. 9, 2007, now Pat. No. 7,695,928.

(60) Provisional application No. 60/790,673, filed on Apr. 10, 2006.

(51) Int. Cl.
*G01N 33/53* (2006.01)
*C12P 21/02* (2006.01)
*A61K 38/04* (2006.01)
*A61K 38/00* (2006.01)

(52) U.S. Cl. ......... 435/7.8; 435/69.7; 435/7.1; 530/327; 530/324; 530/329

(58) Field of Classification Search .................. None
See application file for complete search history.

(56) References Cited

U.S. PATENT DOCUMENTS 4,567,162 A    1/1986   de Castiglione et al.
6,610,836 B1 *  8/2003   Breton et al. ............. 536/23.1

FOREIGN PATENT DOCUMENTS

| EP | 0134986 | 3/1985 |
| EP | 0183245 | 6/1986 |
| WO | 02/090544 A2 | 11/2002 |
| WO | 03/004604 A2 | 1/2003 |
| WO | 2006/007542 A1 | 1/2006 |

OTHER PUBLICATIONS

Bezprozvanny et al., "PDZ Domains; evolving classification" *FEBS Letters*, Amsterdam, NL 512(1-3):347-349 (Feb. 13, 2002).
Fuh et al., "Analysis of PDZ domain-ligand interactions using carboxyl-terminal phage display" *Journal of Biological Chemistry, American Society of Biochemical Biologists*, Birmingham, US 275 (28):21486-21491 (Jul. 14, 2000).
Laura et al., "The Erbin PDZ domain binds with high affinity and specificity to the carboxyl termini of delta-catenin and ARVCF" *Journal of Biological Chemistry, American Society of Biochemical Biologists*, Birmingham, US 277(15):12906-12914 (Jan. 30, 2002).
Murthy et al., "Fusion proteins could generate false positives in peptide phage display" *BioTechniques* 26(1):142-149 (Jan. 1999).
Skelton et al., "Origins of PDZ domain ligand specificity. Structure determination and mutagents of the Erbin PDZ domain" *Journal of Biological Chemistry* 278 (9):7645-7654 (Feb. 28, 2003).
Wiedemann et al., "Quantification of PDZ Domain Specificity, Prediction of Ligand Affinity and Rational Design of Super-binding Peptides" *Journal of Molecular Biology*, London, GB 343(3):703-718 (Oct. 22, 2004).
Wong et al., "Direct binding of the PDZ domain of Dishevelled to a conserved internal sequence in the C-terminal region of Frizzled" *Molecular Cell* 12(5):1251-1260 (Nov. 2003).
PCT/IPEA International Preliminary Examination Report on Patentability for WO 2007/121147 (Apr. 16, 2008).
PCT/ISA International Search Report for WO 2007/121147 (Oct. 27, 2007).

* cited by examiner

*Primary Examiner* — Shulamith H Shafer

(57) ABSTRACT

The invention provides modulators of Dvl PDZ-ligand interaction, and methods of identifying and using these modulators.

15 Claims, 8 Drawing Sheets

FIG._1A

| POS | -9 | -8 | -7 | -6 | -5 | -4 | -3 | -2 | -1 | 0 |
|---|---|---|---|---|---|---|---|---|---|---|
| | S | W | W | N | K | C | Y | G | W | F |
| | N | K | R | Y | T | V | L | G | W | F |
| | I | V | R | W | T | L | L | G | I | F |
| | T | S | S | W | K | W | Y | G | W | L |
| | P | R | I | F | K | D | Y | G | M | F |
| | Y | W | T | R | T | F | Y | G | F | F |
| | | N | R | W | R | L | L | G | W | F |
| | T | S | W | C | K | W | Y | G | W | L |
| | F | W | I | Y | K | Y | Y | G | R | F |
| | | D | R | I | R | F | L | G | W | F |
| | A | V | R | W | L | F | L | G | W | F |
| | R | S | G | H | R | F | L | G | W | F |
| | | | S | W | K | L | L | G | F | F |
| | T | S | F | L | K | G | Y | G | W | L |
| | S | I | S | Y | W | F | Y | G | W | L |
| | L | L | F | L | K | Y | Y | G | W | L |
| | S | T | R | H | Y | R | T | W | W | F |
| | | N | V | F | R | F | L | G | W | L |
| | | | T | W | R | V | L | G | W | F |
| | | | N | W | K | W | Y | G | F | F |
| | | | | Y | T | F | F | G | W | F |
| | | S | H | F | K | F | F | G | W | F |
| | | N | R | I | P | C | L | G | G | W |
| | S | P | R | F | T | F | L | G | W | F |
| | R | I | V | S | F | F | Y | G | W | L |
| | | | | | K | F | L | G | W | F |
| | | | | Y | F | F | Y | G | W | F |
| | T | P | L | Y | N | Y | F | G | G | L |
| | T | V | R | W | V | F | F | G | F | F |
| | R | T | R | F | T | C | F | G | W | F |
| | M | T | K | W | I | W | Y | G | W | L |
| | R | I | S | W | T | F | L | G | Y | F |
| | R | P | F | C | T | F | L | G | W | F |
| | S | W | Y | F | K | F | Y | G | W | L |
| | I | T | R | Y | T | F | F | G | F | F |

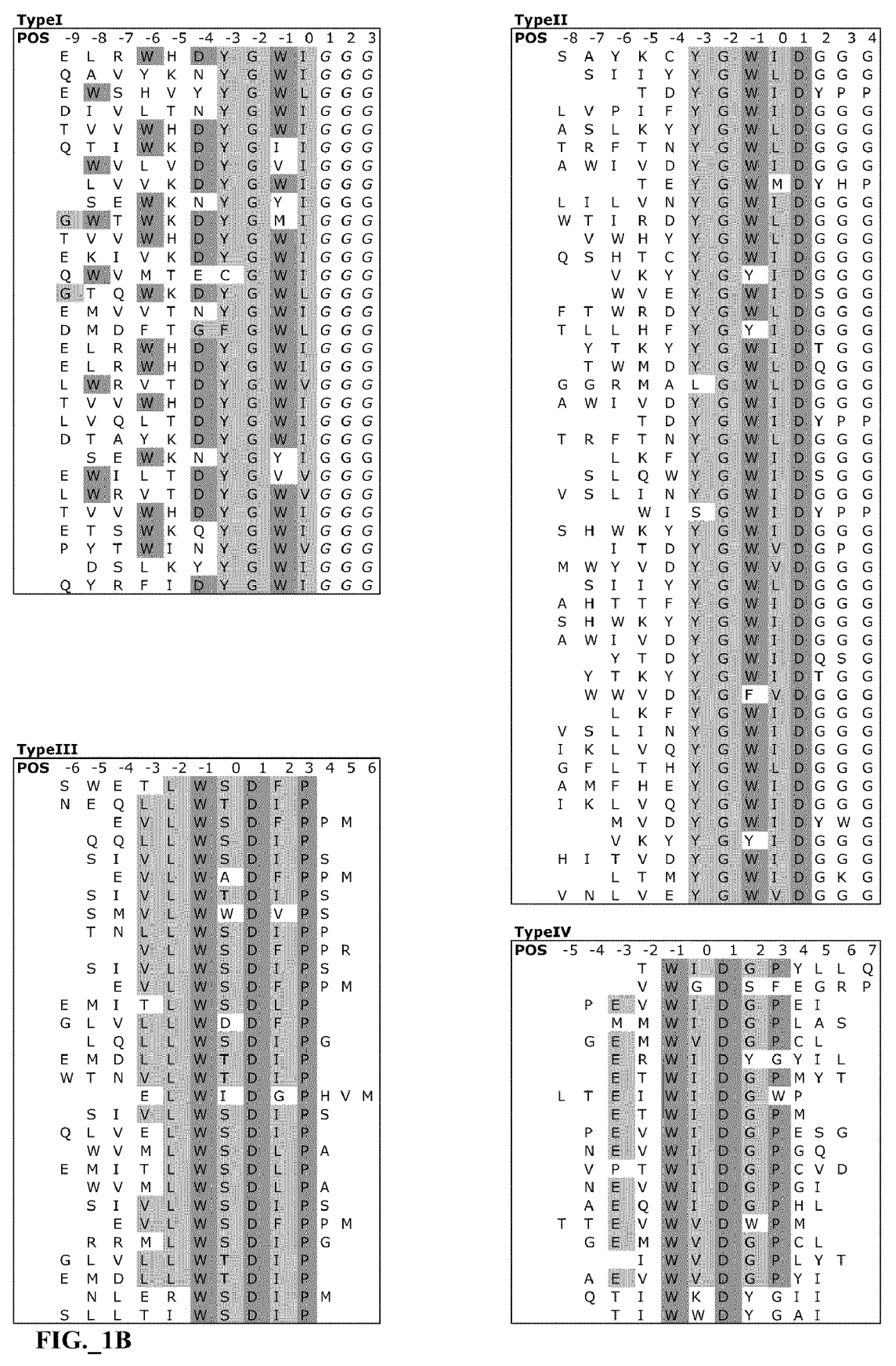

```
hDvl1   D A           V       RHH        D                    60
hDvl2   E T           V       KYN        E                    60
hDvl3   E S           T       KYN        E                    60
wDsh-1  ----AA    S  DVI  N  DTVN    TSNC N   VAN             56 hDvl1         DVI             E  SQT   S           T ----    112
hDvl2         DM              E  HKP   V           S ----    112
hDvl3         FT              E  HKP   T             ----    112
wDsh-1     A     TS  FT Q  D   A SRR   K    SFENGQSCFT        112
```

B.

Figure 3
A.
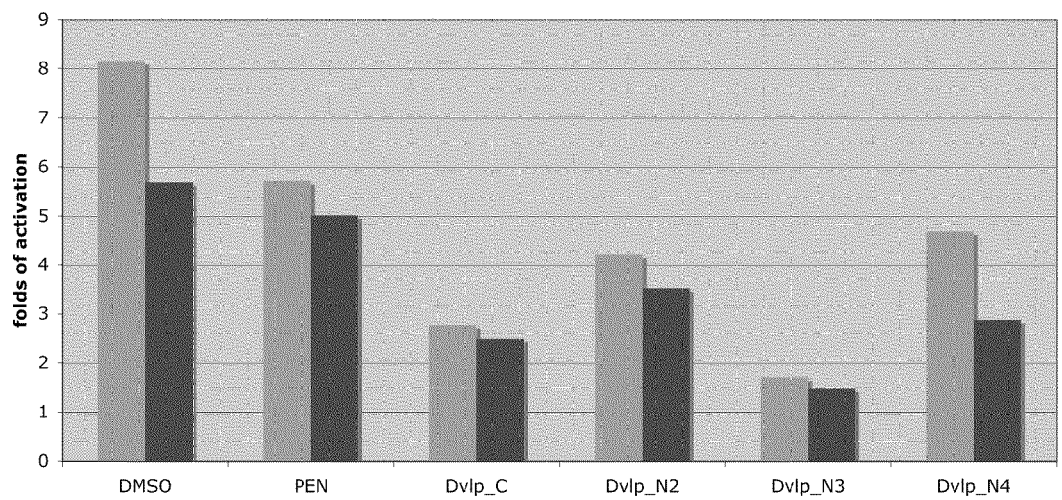
B.
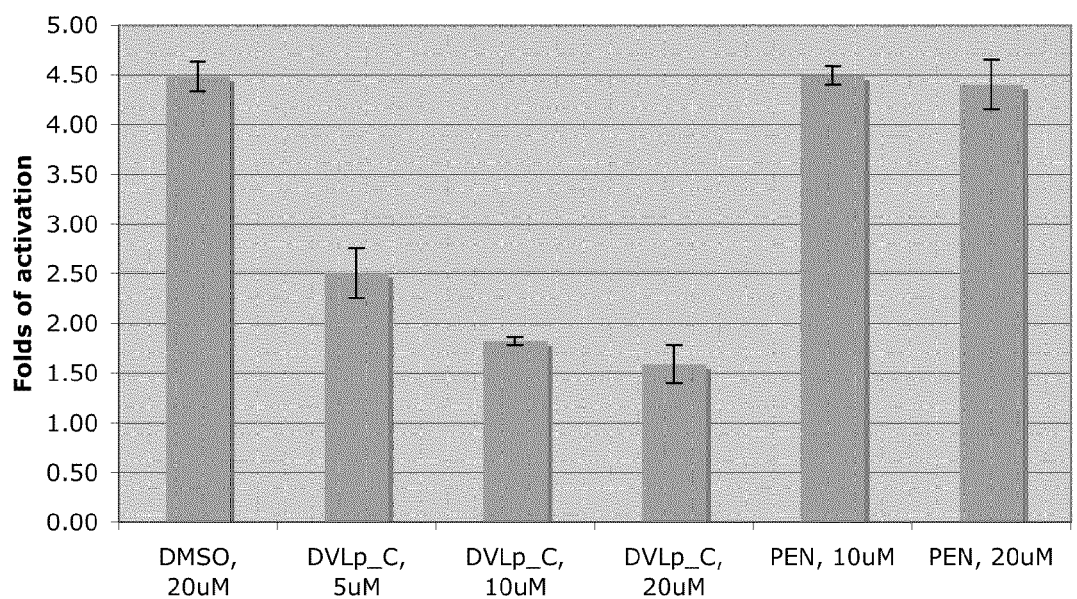

C.
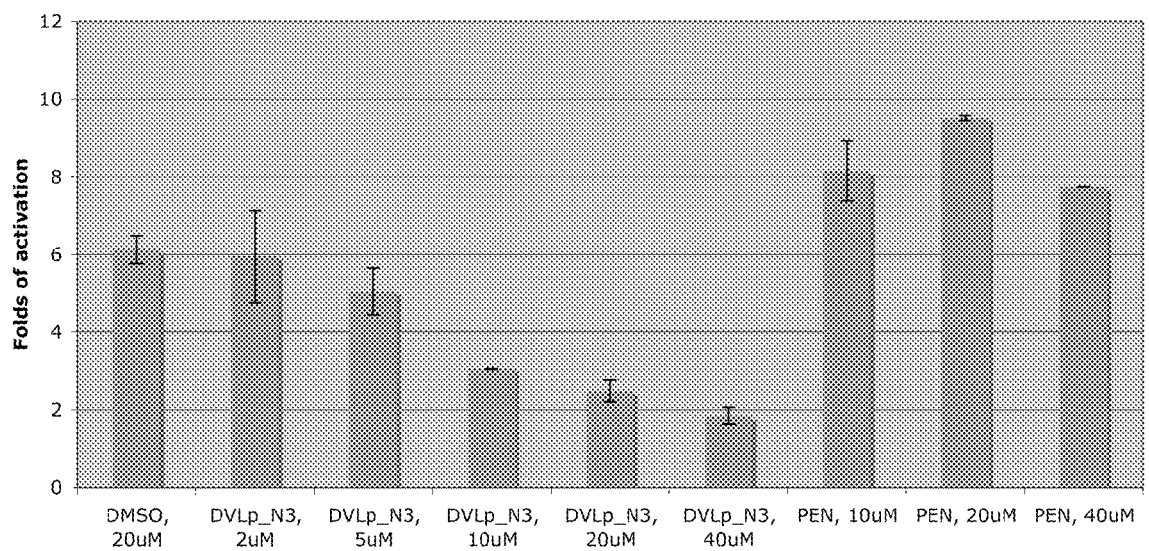
D.
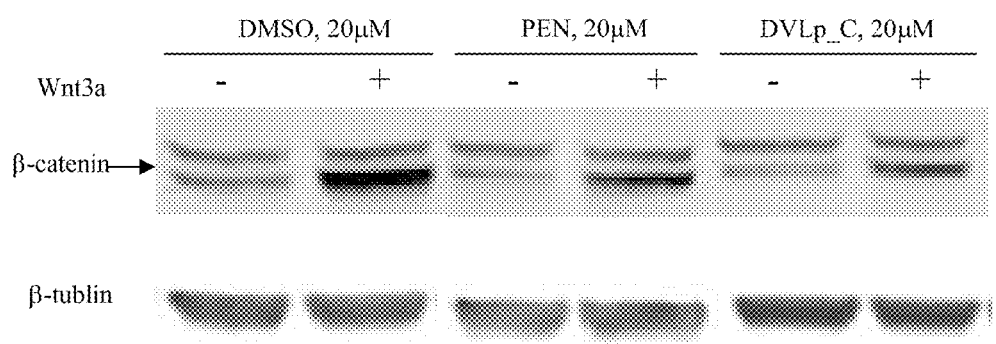
E.
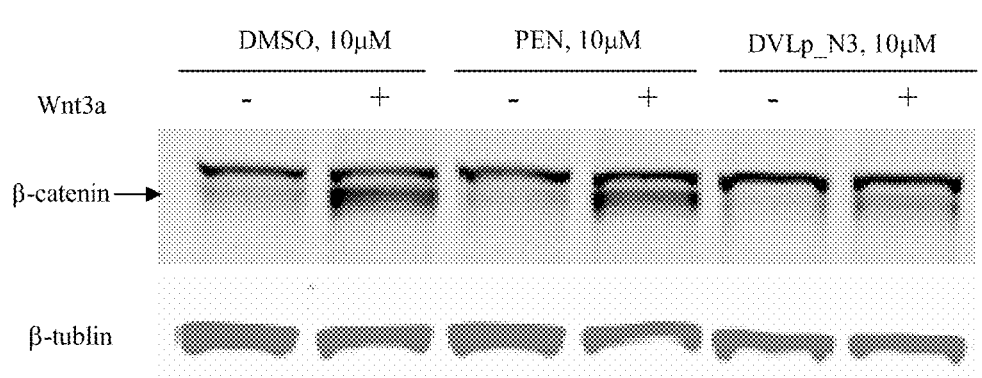

A.

B.
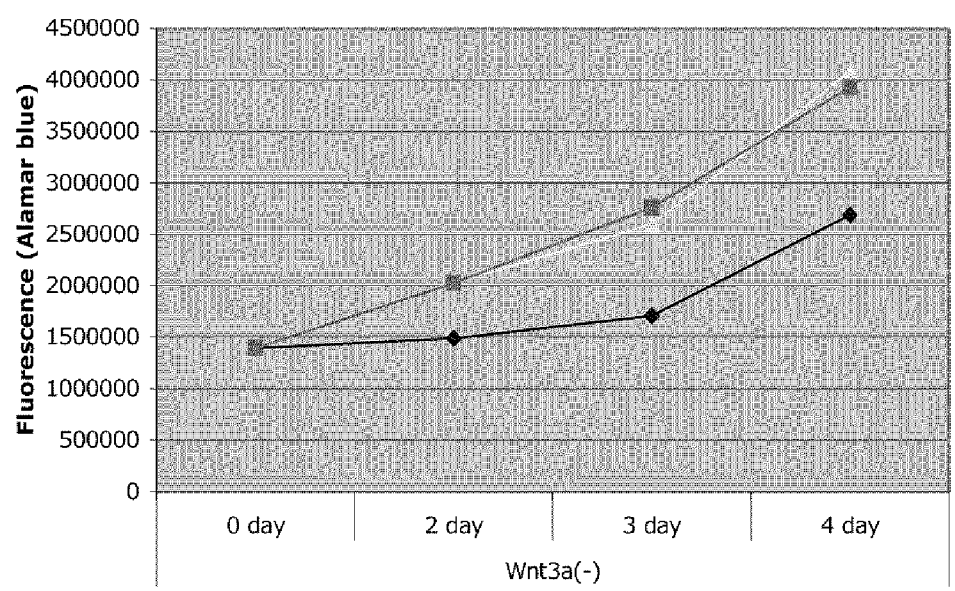

SEQUENCE LISTING

<160> NUMBER OF SEQ ID NOS: 208

<210> SEQ ID NO 1
<211> LENGTH: 112
<212> TYPE: PRT
<213> ORGANISM: Homo sapiens

<400> SEQUENCE: 1

```
Asp Arg Ala Ser Ser Phe Ser Ser Ile Thr Asp Ser Thr Met Ser Leu
1               5                   10                  15

Asn Ile Val Thr Val Thr Leu Asn Met Glu Arg His His Phe Leu Gly
            20                  25                  30

Ile Ser Ile Val Gly Gln Ser Asn Asp Arg Gly Asp Gly Ile Tyr
        35                  40                  45

Ile Gly Ser Ile Met Lys Gly Ala Val Ala Ala Asp Gly Arg Ile
        50                  55                  60

Glu Pro Gly Asp Met Leu Leu Gln Val Asn Asp Val Asn Phe Glu Asn
65                  70                  75                  80

Met Ser Asn Asp Asp Ala Val Arg Val Leu Arg Glu Ile Val Ser Gln
            85                  90                  95

Thr Gly Pro Ile Ser Leu Thr Val Ala Lys Cys Trp Asp Pro Thr Pro
            100                 105                 110
```

<210> SEQ ID NO 2
<211> LENGTH: 112
<212> TYPE: PRT
<213> ORGANISM: Homo sapiens

<400> SEQUENCE: 2

```
Glu Arg Thr Ser Ser Phe Ser Ser Val Thr Asp Ser Thr Met Ser Leu
1               5                   10                  15

Asn Ile Ile Thr Val Thr Leu Asn Met Glu Lys Tyr Asn Phe Leu Gly
            20                  25                  30

Ile Ser Ile Val Gly Gln Ser Asn Glu Arg Gly Asp Gly Gly Ile Tyr
        35                  40                  45

Ile Gly Ser Ile Met Lys Gly Ala Val Ala Ala Asp Gly Arg Ile
        50                  55                  60

Glu Pro Gly Asp Met Leu Leu Gln Val Asn Asp Met Asn Phe Glu Asn
65                  70                  75                  80

Met Ser Asn Asp Asp Ala Val Arg Val Leu Arg Asp Ile Val His Lys
            85                  90                  95

Pro Gly Pro Ile Val Leu Thr Val Ala Lys Cys Trp Asp Pro Ser Pro
            100                 105                 110
```

<210> SEQ ID NO 3
<211> LENGTH: 112
<212> TYPE: PRT
<213> ORGANISM: Homo sapiens -continued

```
<400> SEQUENCE: 3

Glu Arg Ser Ser Ser Phe Ser Ser Ile Thr Asp Ser Thr Met Ser Leu
1               5                   10                  15

Asn Ile Ile Thr Val Thr Leu Asn Met Glu Lys Tyr Asn Phe Leu Gly
            20                  25                  30

Ile Ser Ile Val Gly Gln Ser Asn Glu Arg Gly Asp Gly Gly Ile Tyr
        35                  40                  45

Ile Gly Ser Ile Met Lys Gly Gly Ala Val Ala Ala Asp Gly Arg Ile
    50                  55                  60

Glu Pro Gly Asp Met Leu Leu Gln Val Asn Glu Ile Asn Phe Glu Asn
65                  70                  75                  80

Met Ser Asn Asp Ala Val Arg Val Leu Arg Glu Ile Val His Lys
                85                  90                  95

Pro Gly Pro Ile Thr Leu Thr Val Ala Lys Cys Trp Asp Pro Ser Pro
            100                 105                 110

<210> SEQ ID NO 4
<211> LENGTH: 112
<212> TYPE: PRT
<213> ORGANISM: Caenorhabditis sp.

<400> SEQUENCE: 4

Ala Ala Ser Ser Ile Thr Glu Ser Ser Met Ser Leu Asp Val Ile Thr
1               5                   10                  15

Val Asn Leu Asn Met Asp Thr Val Asn Phe Leu Gly Ile Ser Ile Val
            20                  25                  30

Gly Gln Thr Ser Asn Cys Gly Asp Asn Gly Ile Tyr Val Ala Asn Ile
        35                  40                  45

Met Lys Gly Gly Ala Val Ala Leu Asp Gly Arg Ile Glu Ala Gly Asp
    50                  55                  60

Met Ile Leu Gln Val Asn Glu Thr Ser Phe Glu Asn Phe Thr Asn Asp
65                  70                  75                  80

Gln Ala Val Asp Val Leu Arg Glu Ala Val Ser Arg Arg Gly Pro Ile
                85                  90                  95

Lys Leu Thr Val Ala Lys Ser Phe Glu Asn Gly Gln Ser Cys Phe Thr
            100                 105                 110

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Trp Trp Asn Lys Cys Tyr Gly Trp Phe
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Lys Arg Tyr Thr Val Leu Gly Trp Phe
1               5                   10
```

-continued

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Val Arg Trp Thr Leu Leu Gly Ile Phe
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Ser Ser Trp Lys Trp Tyr Gly Trp Leu
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Arg Ile Phe Lys Asp Tyr Gly Met Phe
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Trp Thr Arg Thr Phe Tyr Gly Phe Phe
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Arg Trp Arg Leu Leu Gly Trp Phe
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 12

Thr Ser Trp Cys Lys Trp Tyr Gly Trp Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Trp Ile Tyr Lys Tyr Tyr Gly Arg Phe
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Arg Ile Arg Phe Leu Gly Trp Phe
1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Val Arg Trp Leu Phe Leu Gly Trp Phe
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Gly His Arg Phe Leu Gly Trp Phe
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Trp Lys Leu Leu Gly Phe Phe
1               5

<210> SEQ ID NO 18
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 18

Thr Ser Phe Leu Lys Gly Tyr Gly Trp Leu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Ile Ser Tyr Trp Phe Tyr Gly Trp Leu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Leu Phe Leu Lys Tyr Tyr Gly Trp Leu
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Thr Arg His Tyr Arg Thr Trp Trp Phe
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asn Val Phe Arg Phe Phe Gly Trp Leu
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Trp Arg Val Leu Gly Trp Phe
1               5
```

```
<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asn Trp Lys Trp Tyr Gly Phe Phe
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Thr Phe Phe Gly Trp Phe
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser His Phe Lys Phe Phe Gly Trp Phe
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Arg Ile Pro Cys Leu Gly Gly Trp
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Pro Arg Phe Thr Phe Leu Gly Trp Phe
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29
```

Arg Ile Val Ser Phe Phe Tyr Gly Trp Leu
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Phe Leu Gly Trp Phe
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Phe Phe Tyr Gly Trp Phe
1               5

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Pro Leu Tyr Asn Tyr Phe Gly Gly Leu
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Val Arg Trp Val Phe Phe Gly Phe Phe
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Thr Arg Phe Thr Cys Phe Gly Trp Phe
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic

```
                                     -continued
      peptide

<400> SEQUENCE: 35

Met Thr Lys Trp Ile Trp Tyr Gly Trp Leu
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ile Ser Trp Thr Phe Leu Gly Tyr Phe
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Pro Phe Cys Thr Phe Leu Gly Trp Phe
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Trp Tyr Phe Lys Phe Tyr Gly Trp Leu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Thr Arg Tyr Thr Phe Phe Gly Phe Phe
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Leu Arg Trp His Asp Tyr Gly Trp Ile Gly Gly Gly
1               5                   10

<210> SEQ ID NO 41
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Ala Val Tyr Lys Asn Tyr Gly Trp Ile Gly Gly Gly
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Trp Ser His Val Tyr Tyr Gly Trp Leu Gly Gly Gly
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Ile Val Leu Thr Asn Tyr Gly Trp Ile Gly Gly Gly
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Val Val Trp His Asp Tyr Gly Trp Ile Gly Gly Gly
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Thr Ile Trp Lys Asp Tyr Gly Ile Ile Gly Gly Gly
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Trp Val Leu Val Asp Tyr Gly Val Ile Gly Gly Gly
1               5                   10
```

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Val Val Lys Asp Tyr Gly Trp Ile Gly Gly Gly
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Glu Trp Lys Asn Tyr Gly Tyr Ile Gly Gly Gly
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Trp Thr Trp Lys Asp Tyr Gly Met Ile Gly Gly Gly
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Val Val Trp His Asp Tyr Gly Trp Ile Gly Gly Gly
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Lys Ile Val Lys Asp Tyr Gly Trp Ile Gly Gly Gly
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 52

Gln Trp Val Met Thr Glu Cys Gly Trp Ile Gly Gly Gly
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Thr Gln Trp Lys Asp Tyr Gly Trp Leu Gly Gly Gly
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Met Val Val Thr Asn Tyr Gly Trp Ile Gly Gly Gly
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Met Asp Phe Thr Gly Phe Gly Trp Leu Gly Gly Gly
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Leu Arg Trp His Asp Tyr Gly Trp Ile Gly Gly Gly
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Leu Arg Trp His Asp Tyr Gly Trp Ile Gly Gly Gly
1               5                   10

<210> SEQ ID NO 58
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 58

Leu Trp Arg Val Thr Asp Tyr Gly Trp Val Gly Gly Gly
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Val Val Trp His Asp Tyr Gly Trp Ile Gly Gly Gly
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Val Gln Leu Thr Asp Tyr Gly Trp Ile Gly Gly Gly
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp Thr Ala Tyr Lys Asp Tyr Gly Trp Ile Gly Gly Gly
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Glu Trp Lys Asn Tyr Gly Tyr Ile Gly Gly Gly
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Glu Trp Ile Leu Thr Asp Tyr Gly Val Val Gly Gly Gly
1               5                   10
```

```
<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Trp Arg Val Thr Asp Tyr Gly Trp Val Gly Gly Gly
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Val Val Trp His Asp Tyr Gly Trp Ile Gly Gly Gly
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Thr Ser Trp Lys Gln Tyr Gly Trp Ile Gly Gly Gly
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Pro Tyr Thr Trp Ile Asn Tyr Gly Trp Val Gly Gly Gly
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Ser Leu Lys Tyr Tyr Gly Trp Ile Gly Gly Gly
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69
```

```
Gln Tyr Arg Phe Ile Asp Tyr Gly Trp Ile Gly Gly Gly
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Ala Tyr Lys Cys Tyr Gly Trp Ile Asp Gly Gly Gly
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Ile Ile Tyr Tyr Gly Trp Leu Asp Gly Gly Gly
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Asp Tyr Gly Trp Ile Asp Tyr Pro Pro
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Val Pro Ile Phe Tyr Gly Trp Ile Asp Gly Gly Gly
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Ser Leu Lys Tyr Tyr Gly Trp Leu Asp Gly Gly Gly
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
```

-continued

```
<400> SEQUENCE: 75

Thr Arg Phe Thr Asn Tyr Gly Trp Leu Asp Gly Gly Gly
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Trp Ile Val Asp Tyr Gly Trp Ile Asp Gly Gly Gly
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Thr Glu Tyr Gly Trp Met Asp Tyr His Pro
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Ile Leu Val Asn Tyr Gly Trp Ile Asp Gly Gly Gly
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Thr Ile Arg Asp Tyr Gly Trp Leu Asp Gly Gly Gly
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Val Trp His Tyr Tyr Gly Trp Leu Asp Gly Gly Gly
1               5                   10

<210> SEQ ID NO 81
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Ser His Thr Cys Tyr Gly Trp Ile Asp Gly Gly Gly
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Val Lys Tyr Tyr Gly Tyr Ile Asp Gly Gly Gly
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Trp Val Glu Tyr Gly Trp Ile Asp Ser Gly Gly
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Phe Thr Trp Arg Asp Tyr Gly Trp Leu Asp Gly Gly Gly
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Leu Leu His Phe Tyr Gly Tyr Ile Asp Gly Gly Gly
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Tyr Thr Lys Tyr Tyr Gly Trp Ile Asp Thr Gly Gly
1               5                   10
```

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Trp Met Asp Tyr Gly Trp Leu Asp Gln Gly Gly
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Gly Arg Met Ala Leu Gly Trp Leu Asp Gly Gly Gly
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Trp Ile Val Asp Tyr Gly Trp Ile Asp Gly Gly Gly
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Thr Asp Tyr Gly Trp Ile Asp Tyr Pro Pro
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Thr Arg Phe Thr Asn Tyr Gly Trp Leu Asp Gly Gly Gly
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Leu Lys Phe Tyr Gly Trp Ile Asp Gly Gly Gly
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Leu Gln Trp Tyr Gly Trp Ile Asp Ser Gly Gly
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Val Ser Leu Ile Asn Tyr Gly Trp Ile Asp Gly Gly Gly
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Trp Ile Ser Gly Trp Ile Asp Tyr Pro Pro
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser His Trp Lys Tyr Tyr Gly Trp Ile Asp Gly Gly Gly
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ile Thr Asp Tyr Gly Trp Val Asp Gly Pro Gly
1               5                   10

<210> SEQ ID NO 98
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 98

Met Trp Tyr Val Asp Tyr Gly Trp Val Asp Gly Gly Gly
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Ile Ile Tyr Tyr Gly Trp Leu Asp Gly Gly Gly
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala His Thr Thr Phe Tyr Gly Trp Ile Asp Gly Gly Gly
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser His Trp Lys Tyr Tyr Gly Trp Ile Asp Gly Gly Gly
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Trp Ile Val Asp Tyr Gly Trp Ile Asp Gly Gly Gly
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Thr Asp Tyr Gly Trp Ile Asp Gln Ser Gly
1               5                   10
```

```
<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Tyr Thr Lys Tyr Tyr Gly Trp Ile Asp Thr Gly Gly
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Trp Trp Val Asp Tyr Gly Phe Val Asp Gly Gly Gly
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Leu Lys Phe Tyr Gly Trp Ile Asp Gly Gly Gly
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Val Ser Leu Ile Asn Tyr Gly Trp Ile Asp Gly Gly Gly
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ile Lys Leu Val Gln Tyr Gly Trp Ile Asp Gly Gly Gly
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109
```

```
Gly Phe Leu Thr His Tyr Gly Trp Leu Asp Gly Gly Gly
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Met Phe His Glu Tyr Gly Trp Ile Asp Gly Gly Gly
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ile Lys Leu Val Gln Tyr Gly Trp Ile Asp Gly Gly Gly
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Met Val Asp Tyr Gly Trp Ile Asp Tyr Trp Gly
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Val Lys Tyr Tyr Gly Tyr Ile Asp Gly Gly Gly
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

His Ile Thr Val Asp Tyr Gly Trp Ile Asp Gly Gly Gly
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 115

Leu Thr Met Tyr Gly Trp Ile Asp Gly Lys Gly
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Val Asn Leu Val Glu Tyr Gly Trp Val Asp Gly Gly Gly
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Trp Glu Thr Leu Trp Ser Asp Phe Pro
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asn Glu Gln Leu Leu Trp Thr Asp Ile Pro
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Glu Val Leu Trp Ser Asp Phe Pro Pro Met
1               5                   10

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Gln Leu Leu Trp Ser Asp Ile Pro
1               5

<210> SEQ ID NO 121
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Ile Val Leu Trp Ser Asp Ile Pro Ser
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Glu Val Leu Trp Ala Asp Phe Pro Pro Met
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Ile Val Leu Trp Thr Asp Ile Pro Ser
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Met Val Leu Trp Trp Asp Val Pro Ser
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Thr Asn Leu Leu Trp Ser Asp Ile Pro Pro
1               5                   10

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Val Leu Trp Ser Asp Phe Pro Pro Arg
1               5
```

```
<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ser Ile Val Leu Trp Ser Asp Ile Pro Ser
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Glu Val Leu Trp Ser Asp Phe Pro Pro Met
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Glu Met Ile Thr Leu Trp Ser Asp Leu Pro
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Leu Val Leu Leu Trp Asp Asp Phe Pro
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Leu Gln Leu Leu Trp Ser Asp Ile Pro Gly
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 132

Glu Met Asp Leu Leu Trp Thr Asp Ile Pro
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Trp Thr Asn Val Leu Trp Thr Asp Ile Pro
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Glu Leu Trp Ile Asp Gly Pro His Val Met
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ser Ile Val Leu Trp Ser Asp Ile Pro Ser
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Leu Val Glu Leu Trp Ser Asp Ile Pro
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Trp Val Met Leu Trp Ser Asp Leu Pro Ala
1               5                   10

<210> SEQ ID NO 138
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 138

Glu Met Ile Thr Leu Trp Ser Asp Leu Pro
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Trp Val Met Leu Trp Ser Asp Leu Pro Ala
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ser Ile Val Leu Trp Ser Asp Ile Pro Ser
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Glu Val Leu Trp Ser Asp Phe Pro Pro Met
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Arg Arg Met Leu Trp Ser Asp Ile Pro Gly
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Leu Val Leu Leu Trp Thr Asp Ile Pro
1               5                   10
```

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Glu Met Asp Leu Leu Trp Thr Asp Ile Pro
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asn Leu Glu Arg Trp Ser Asp Ile Pro Met
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Leu Leu Thr Ile Trp Ser Asp Ile Pro
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Thr Trp Ile Asp Gly Pro Tyr Leu Leu Gln
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Val Trp Gly Asp Ser Phe Glu Gly Arg Pro
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

```
Pro Glu Val Trp Ile Asp Gly Pro Glu Ile
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Met Met Trp Ile Asp Gly Pro Leu Ala Ser
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Glu Met Trp Val Asp Gly Pro Cys Leu
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Glu Arg Trp Ile Asp Tyr Gly Tyr Ile Leu
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Glu Thr Trp Ile Asp Gly Pro Met Tyr Thr
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Leu Thr Glu Ile Trp Ile Asp Gly Trp Pro
1               5                   10

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 155

Glu Thr Trp Ile Asp Gly Pro Met
1               5

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Pro Glu Val Trp Ile Asp Gly Pro Glu Ser Gly
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asn Glu Val Trp Ile Asp Gly Pro Gly Gln
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Val Pro Thr Trp Ile Asp Gly Pro Cys Val Asp
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asn Glu Val Trp Ile Asp Gly Pro Gly Ile
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Glu Gln Trp Ile Asp Gly Pro His Leu
1               5                   10

<210> SEQ ID NO 161
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Thr Thr Glu Val Trp Val Asp Trp Pro Met
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Glu Met Trp Val Asp Gly Pro Cys Leu
1               5                   10

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ile Trp Val Asp Gly Pro Leu Tyr Thr
1               5

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ala Glu Val Trp Val Asp Gly Pro Tyr Ile
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gln Thr Ile Trp Lys Asp Tyr Gly Ile Ile
1               5                   10

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Thr Ile Trp Trp Asp Tyr Gly Ala Ile
1               5
```

```
<210> SEQ ID NO 167
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Asp Gly Gly Gly
1

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Val

<400> SEQUENCE: 168

Trp Xaa Asp Gly Pro
1               5

<210> SEQ ID NO 169
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Lys Trp Tyr Gly Trp Leu
1               5

<210> SEQ ID NO 170
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Tyr Ala Lys Gly Phe Gly Met Leu
1               5

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Glu Ile Val Leu Trp Ser Asp Ile Pro Gly
1               5                   10

<210> SEQ ID NO 172
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 172

Arg Gln Ile Lys Ile Trp Phe Gln Asn Arg Arg Met Lys Trp Lys Lys
1               5                   10                  15

<210> SEQ ID NO 173
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Arg Gln Ile Lys Ile Trp Phe Gln Asn Arg Arg Met Lys Trp Lys Lys
1               5                   10                  15

Lys Trp Tyr Gly Trp Leu
            20

<210> SEQ ID NO 174
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Arg Gln Ile Lys Ile Trp Phe Gln Asn Arg Arg Met Lys Trp Lys Lys
1               5                   10                  15

Gly Trp Lys Asp Tyr Gly Trp Ile Asp Gly
            20                  25

<210> SEQ ID NO 175
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Arg Gln Ile Lys Ile Trp Phe Gln Asn Arg Arg Met Lys Lys Gly Glu
1               5                   10                  15

Ile Val Leu Trp Ser Asp Ile Pro Gly
            20                  25

<210> SEQ ID NO 176
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Arg Gln Ile Lys Ile Trp Phe Gln Asn Arg Arg Met Lys Trp Lys Lys
1               5                   10                  15

Gly Ser Gly Asn Glu Val Trp Ile Asp Gly Pro Gly
            20                  25

<210> SEQ ID NO 177
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Lys Trp Tyr Gly Trp Phe
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Trp Lys Trp Tyr Gly Trp Leu
1               5

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Trp Lys Trp Tyr Gly Trp Phe
1               5

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Trp Lys Asp Tyr Gly Trp Ile Asp Gly
1               5                   10

<210> SEQ ID NO 181
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(28)
<223> OTHER INFORMATION: a, c, g, or t
<220> FEATURE:
<221> NAME/KEY: modified_base
<222> LOCATION: (30)..(31)
<223> OTHER INFORMATION: a, c, g, or t
<220> FEATURE:
<221> NAME/KEY: modified_base
<222> LOCATION: (33)..(34)
<223> OTHER INFORMATION: a, c, g, or t
<220> FEATURE:
<221> NAME/KEY: modified_base
<222> LOCATION: (36)..(37)
<223> OTHER INFORMATION: a, c, g, or t
<220> FEATURE:
<221> NAME/KEY: modified_base
<222> LOCATION: (39)..(40)
```

```
<223> OTHER INFORMATION: a, c, g, or t
<220> FEATURE:
<221> NAME/KEY: modified_base
<222> LOCATION: (42)..(43)
<223> OTHER INFORMATION: a, c, g, or t
<220> FEATURE:
<221> NAME/KEY: modified_base
<222> LOCATION: (45)..(46)
<223> OTHER INFORMATION: a, c, g, or t
<220> FEATURE:
<221> NAME/KEY: modified_base
<222> LOCATION: (48)..(49)
<223> OTHER INFORMATION: a, c, g, or t
<220> FEATURE:
<221> NAME/KEY: modified_base
<222> LOCATION: (51)..(52)
<223> OTHER INFORMATION: a, c, g, or t
<220> FEATURE:
<221> NAME/KEY: modified_base
<222> LOCATION: (54)..(55)
<223> OTHER INFORMATION: a, c, g, or t

<400> SEQUENCE: 181
acatcgacag cgcccccggt ggcggannkn nknnknnknn knnknnknnk nnknnktgat      60
aaaccgatac a                                                          71

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Gly Gly Lys Trp Tyr Gly Trp Leu
1               5

<210> SEQ ID NO 183
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Lys Gly Phe Gly Met Leu
1               5

<210> SEQ ID NO 184
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: Y, L, F, or I
<220> FEATURE:
<221> NAME/KEY: MISC_FEATURE
<222> LOCATION: (3)..(3)
<223> OTHER INFORMATION: W, M, F, or Y
<220> FEATURE:
<221> NAME/KEY: MISC_FEATURE
<222> LOCATION: (4)..(4)
<223> OTHER INFORMATION: F or L

<400> SEQUENCE: 184

Xaa Gly Xaa Xaa
```

```
<210> SEQ ID NO 185
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: Y, C, L, F, or S
<220> FEATURE:
<221> NAME/KEY: MISC_FEATURE
<222> LOCATION: (3)..(3)
<223> OTHER INFORMATION: W, M, F, I, V, or Y
<220> FEATURE:
<221> NAME/KEY: MISC_FEATURE
<222> LOCATION: (4)..(4)
<223> OTHER INFORMATION: I, V, M, or L

<400> SEQUENCE: 185

Xaa Gly Xaa Xaa
1

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: any naturally occuring amino acid
<220> FEATURE:
<221> NAME/KEY: MISC_FEATURE
<222> LOCATION: (2)..(2)
<223> OTHER INFORMATION: any naturally occuring amino acid
<220> FEATURE:
<221> NAME/KEY: MISC_FEATURE
<222> LOCATION: (4)..(4)
<223> OTHER INFORMATION: S, T, A, W, D, or I
<220> FEATURE:
<221> NAME/KEY: MISC_FEATURE
<222> LOCATION: (6)..(6)
<223> OTHER INFORMATION: F, I, V, L, or G

<400> SEQUENCE: 186

Xaa Xaa Trp Xaa Asp Xaa Pro
1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: any naturally occuring amino acid
<220> FEATURE:
<221> NAME/KEY: MISC_FEATURE
<222> LOCATION: (2)..(2)
<223> OTHER INFORMATION: any naturally occuring amino acid
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
```

```
<222> LOCATION: (6)..(6)
<223> OTHER INFORMATION: I, F, or L

<400> SEQUENCE: 187

Xaa Xaa Trp Xaa Asp Xaa Pro
1               5

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: L or V
<220> FEATURE:
<221> NAME/KEY: MISC_FEATURE
<222> LOCATION: (2)..(2)
<223> OTHER INFORMATION: any naturally occuring amino acid
<220> FEATURE:
<221> NAME/KEY: MISC_FEATURE
<222> LOCATION: (4)..(4)
<223> OTHER INFORMATION: S, T, A, W, D, or I
<220> FEATURE:
<221> NAME/KEY: MISC_FEATURE
<222> LOCATION: (6)..(6)
<223> OTHER INFORMATION: F, I, V, L, or G

<400> SEQUENCE: 188

Xaa Xaa Trp Xaa Asp Xaa Pro
1               5

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: any naturally occuring amino acid
<220> FEATURE:
<221> NAME/KEY: MISC_FEATURE
<222> LOCATION: (4)..(4)
<223> OTHER INFORMATION: S, T, A, W, D, or I
<220> FEATURE:
<221> NAME/KEY: MISC_FEATURE
<222> LOCATION: (6)..(6)
<223> OTHER INFORMATION: F, I, V, L, or G

<400> SEQUENCE: 189

Xaa Leu Trp Xaa Asp Xaa Pro
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: any naturally occuring amino acid
<220> FEATURE:
<221> NAME/KEY: MISC_FEATURE
<222> LOCATION: (2)..(2)
<223> OTHER INFORMATION: any naturally occuring amino acid
```

```
<220> FEATURE:
<221> NAME/KEY: MISC_FEATURE
<222> LOCATION: (4)..(4)
<223> OTHER INFORMATION: I, G, V, K, or W
<220> FEATURE:
<221> NAME/KEY: MISC_FEATURE
<222> LOCATION: (6)..(6)
<223> OTHER INFORMATION: G, S, Y, or W

<400> SEQUENCE: 190

Xaa Xaa Trp Xaa Asp Xaa Pro
1               5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: any naturally occuring amino acid
<220> FEATURE:
<221> NAME/KEY: MISC_FEATURE
<222> LOCATION: (2)..(2)
<223> OTHER INFORMATION: any naturally occuring amino acid
<220> FEATURE:
<221> NAME/KEY: MISC_FEATURE
<222> LOCATION: (4)..(4)
<223> OTHER INFORMATION: I or V

<400> SEQUENCE: 191

Xaa Xaa Trp Xaa Asp Gly Pro
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(2)
<223> OTHER INFORMATION: any naturally occuring amino acid
<220> FEATURE:
<221> NAME/KEY: MISC_FEATURE
<222> LOCATION: (4)..(4)
<223> OTHER INFORMATION: I, G, V, K, or W
<220> FEATURE:
<221> NAME/KEY: MISC_FEATURE
<222> LOCATION: (6)..(6)
<223> OTHER INFORMATION: G, S, Y, or W

<400> SEQUENCE: 192

Glu Xaa Trp Xaa Asp Xaa Pro
1               5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: any naturally occuring amino acid
<220> FEATURE:
<221> NAME/KEY: MISC_FEATURE
```

-continued

```
<222> LOCATION: (2)..(2)
<223> OTHER INFORMATION: T, V, M, R, I, or Q
<220> FEATURE:
<221> NAME/KEY: MISC_FEATURE
<222> LOCATION: (4)..(4)
<223> OTHER INFORMATION: I, G, V, K, or W
<220> FEATURE:
<221> NAME/KEY: MISC_FEATURE
<222> LOCATION: (6)..(6)
<223> OTHER INFORMATION: G, S, Y, or W

<400> SEQUENCE: 193

Xaa Xaa Trp Xaa Asp Xaa Pro
1               5

<210> SEQ ID NO 194
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: hydrophobic or aromatic amino acid
<220> FEATURE:
<221> NAME/KEY: MISC_FEATURE
<222> LOCATION: (3)..(3)
<223> OTHER INFORMATION: W or Y
<220> FEATURE:
<221> NAME/KEY: MISC_FEATURE
<222> LOCATION: (4)..(4)
<223> OTHER INFORMATION: F or L

<400> SEQUENCE: 194

Xaa Gly Xaa Xaa
1

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(2)
<223> OTHER INFORMATION: any naturally occuring amino acid
<220> FEATURE:
<221> NAME/KEY: MISC_FEATURE
<222> LOCATION: (3)..(3)
<223> OTHER INFORMATION: any naturally occuring amino acid
<220> FEATURE:
<221> NAME/KEY: MISC_FEATURE
<222> LOCATION: (4)..(4)
<223> OTHER INFORMATION: hydrophobic or aromatic amino acid
<220> FEATURE:
<221> NAME/KEY: MISC_FEATURE
<222> LOCATION: (6)..(6)
<223> OTHER INFORMATION: W or Y
<220> FEATURE:
<221> NAME/KEY: MISC_FEATURE
<222> LOCATION: (7)..(7)
<223> OTHER INFORMATION: F or L

<400> SEQUENCE: 195

Trp Xaa Xaa Xaa Gly Xaa Xaa
1               5

<210> SEQ ID NO 196
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (3)..(3)
<223> OTHER INFORMATION: I or V
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: any amino acid

<400> SEQUENCE: 196

Gly Trp Xaa Xaa Xaa Xaa Xaa
1               5

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: I or V
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (8)..(8)
<223> OTHER INFORMATION: any amino acid

<400> SEQUENCE: 197

Tyr Gly Trp Xaa Xaa Xaa Xaa Xaa
1               5

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (3)..(3)
<223> OTHER INFORMATION: I or V
<220> FEATURE:
<221> NAME/KEY: MISC_FEATURE
<222> LOCATION: (7)..(7)
<223> OTHER INFORMATION: any amino acid
```

```
<400> SEQUENCE: 198

Gly Trp Xaa Gly Gly Gly Xaa
1               5

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: I or V
<220> FEATURE:
<221> NAME/KEY: MISC_FEATURE
<222> LOCATION: (8)..(8)
<223> OTHER INFORMATION: any amino acid

<400> SEQUENCE: 199

Tyr Gly Trp Xaa Gly Gly Gly Xaa
1               5

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (3)..(3)
<223> OTHER INFORMATION: I or V

<400> SEQUENCE: 200

Gly Trp Xaa Asp Gly Gly Gly
1               5

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: I or V

<400> SEQUENCE: 201

Tyr Gly Trp Xaa Asp Gly Gly Gly
1               5

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(5)
<223> OTHER INFORMATION: I or V
<220> FEATURE:
<221> NAME/KEY: MISC_FEATURE
<222> LOCATION: (6)..(6)
<223> OTHER INFORMATION: any amino acid
```

```
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (8)..(8)
<223> OTHER INFORMATION: any amino acid
<220> FEATURE:
<221> NAME/KEY: MISC_FEATURE
<222> LOCATION: (9)..(9)
<223> OTHER INFORMATION: any amino acid

<400> SEQUENCE: 202

Asp Tyr Gly Trp Xaa Xaa Xaa Xaa Xaa
1               5

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(2)
<223> OTHER INFORMATION: S or T
<220> FEATURE:
<221> NAME/KEY: MISC_FEATURE
<222> LOCATION: (4)..(4)
<223> OTHER INFORMATION: I, F, or L

<400> SEQUENCE: 203

Trp Xaa Asp Xaa Pro
1               5

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: L or V
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (6)..(6)
<223> OTHER INFORMATION: I, F, or L

<400> SEQUENCE: 204

Xaa Leu Trp Xaa Asp Xaa Pro
1               5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(2)
<223> OTHER INFORMATION: T, V, M, R, I, or Q
<220> FEATURE:
<221> NAME/KEY: MISC_FEATURE
```

```
<222> LOCATION: (4)..(4)
<223> OTHER INFORMATION: I or V

<400> SEQUENCE: 205

Glu Xaa Trp Xaa Asp Gly Pro
1               5

<210> SEQ ID NO 206
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: I or V

<400> SEQUENCE: 206

Tyr Gly Trp Xaa
1

<210> SEQ ID NO 207
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: Y, C, L, F, or S
<220> FEATURE:
<221> NAME/KEY: MISC_FEATURE
<222> LOCATION: (4)..(4)
<223> OTHER INFORMATION: I, V, M, or L

<400> SEQUENCE: 207

Xaa Gly Trp Xaa
1

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(2)
<223> OTHER INFORMATION: Y, C, L, F,or S
<220> FEATURE:
<221> NAME/KEY: MISC_FEATURE
<222> LOCATION: (4)..(4)
<223> OTHER INFORMATION: W, M, F, I, V, or Y
<220> FEATURE:
<221> NAME/KEY: MISC_FEATURE
<222> LOCATION: (5)..(5)
<223> OTHER INFORMATION: I, V, M, or L

<400> SEQUENCE: 208

Asp Xaa Gly Xaa Xaa
1               5
```

DISHEVELED PDZ MODULATORS

CROSS REFERENCE TO RELATED APPLICATIONS

This application is a continuation of U.S. patent application Ser. No. 11/733,146, filed on 9 Apr. 2007, which claims priority under 35 USC §119(e) to U.S. provisional application Ser. No. 60/790,673, filed 10 Apr. 2006, the entire disclosures of which are incorporated herein by reference.

TECHNICAL FIELD

The present invention relates generally to the fields of molecular biology and cell growth regulation. More specifically, the invention concerns modulators of the wnt signaling pathway, and uses of said modulators.

BACKGROUND

Wnt signal pathways are essential for development and have been implicated in tumorigenesis[1]. See also Reya & Clevers, *Nature* (2005), 434:843-850; Logan & Nusse, *Annu. Rev. Cell Dev. Biol.* (2004), 20:781-810; and US 2004/0247593. Disheveled (Dvl) proteins are scaffold proteins that play central role for both canonical and non-canonical Wnt signal pathways[2]. See also Wallingford & Habas, *Development* (2005), 132:4421-4436. Dvl proteins are composed of an N-terminal DIX domain, a central PDZ domain and a C-terminal DEP domain. Of these three, PDZ domain plays the most important role in Wnt signal transduction. Over 20 natural ligands have been reported bound to Dvl PDZ domain (hereinafter "DvlPDZ" or "Dvl PDZ") [2-6], most of which have been indicated to be biologically important for canonical or non-canonical Wnt signal pathways. For example, the direct binding of DvlPDZ to an internal sequence in the C-terminal region of Frizzled has been reported to play an important role in Wnt signal pathway[3]. Over-expression of Dvl protein has been observed in several types of cancers, such as non-small cell lung cancer and mesothelioma [7, 8], making Dvl a drug target for cancer treatment. Efforts have been made to develop specific antagonists to DvlPDZ based on the peptide ligand derived from Dapper and Frizzled[9]. However, the small molecule that was identified reportedly binds to DvlPDZ with very low affinity ($K_i$=237 µM), and the efficacy in vivo has not been fully addressed.

The important cellular functions ascribed to Dvl, in particular those mediated through the protein-protein interaction between DvlPDZ and its ligand(s), suggest that DvlPDZ represents a significant therapeutic target. It would therefore be beneficial to elucidate the mechanistic aspects of DvlPDZ-ligand interaction and provide compositions and methods targeted at modulating its associated functional activities. The present invention provides this and other benefits.

DISCLOSURE OF THE INVENTION

Wnt signal pathways have important biological roles, and its perturbation has been implicated in various cancers. The present invention provides compositions, and methods of using these compositions, for modulating activity of the PDZ domain of the Dvl protein. Because of the important functions associated with Dvl, compositions and methods of the invention present significant clinical utilities. The invention is based in part on extensive analysis and characterization of binding partners (ligands) of Dvl PDZ, said analysis resulting in novel and unexpected findings as described herein.

As described herein, a collection of tight peptide ligands to Dvl PDZ domain were identified using a phage-displayed C-terminal peptide library and N-terminal peptide library. In addition to ligands whose binding motif comprises a required free carboxyl group, the results described herein demonstrate that a subset of Dvl PDZ ligands lacking a free carboxyl terminus are surprisingly capable of binding to Dvl PDZ. Ligands lacking a free carboxyl terminus represent N-terminus and/or internal Dvl PDZ ligand sequences that constitute N-terminal or internal sequences of polypeptides. Characterization of the ligands resulted in the identification of unique binding motifs that are believed to confer molecules with enhanced binding affinity to Dvl PDZ. Exemplary ligands as described herein are useful for screening for modulators of the wnt pathway via modulation of Dvl PDZ activity. Furthermore, such ligands and their derivatives are themselves small molecule drug candidates for treating pathological conditions associated with dysregulation of Wnt signal pathways.

In one aspect, the invention provides molecules capable of specifically binding Dvl PDZ. These molecules are useful in a variety of contexts, for example as modulators of Dvl PDZ-ligand interaction. For example, the invention provides modulator molecules having characteristics that mimic the characteristics of high, low or moderate affinity binders of Dvl PDZ. In one embodiment, the invention provides an isolated polypeptide (e.g., a polypeptide as defined hereinbelow, which specifically includes peptide molecules) that binds specifically to Dvl PDZ, wherein said polypeptide comprises a C-terminal region comprising, consisting, or consisting essentially of a sequence with Gly at position −2, Trp or Tyr at position −1, Phe or Leu at position 0, and a hydrophobic or aromatic residue at position −3, wherein amino acid numbering is based on the C-terminal residue being in position 0 (SEQ ID NO: 194). In one embodiment, position −6 in said C-terminal region is Trp (SEQ ID NO: 195). In one embodiment, position −1 in said C-terminal region is Trp.

In one embodiment, the invention provides an isolated polypeptide (e.g., a polypeptide as defined hereinbelow, which specifically includes peptide molecules) that binds specifically to Dvl PDZ, wherein said polypeptide comprises an N-terminal or internal region comprising, consisting, or consisting essentially of a binding motif comprising Gly-Trp-[Ile or Val]-X1-X2-X3-X4 (SEQ ID NO: 196) or Tyr-Gly-Trp-[Ile or Val]-X1-X2-X3-X4 (SEQ ID NO: 197), wherein Gly is either an N-terminal or internal residue, respectively, and X1, X2, X3 and/or X4 are internal residues. In one embodiment, X1-X2-X3 is G-G-G (SEQ ID NO: 198; SEQ ID NO: 199). In one embodiment, X1-X2-X3-X4 is D-G-G-G (SEQ ID NO: 167; SEQ ID NO: 200; SEQ ID NO: 201). In one embodiment, the Tyr is preceded N-terminally by Asp (SEQ ID NO: 202).

In one embodiment, the invention provides an isolated polypeptide (e.g., a polypeptide as defined hereinbelow, which specifically includes peptide molecules) that binds specifically to Dvl PDZ, wherein said polypeptide comprises an N-terminal or internal region comprising, consisting, or consisting essentially of a binding motif comprising Trp-[Ser or Thr]-Asp-[Ile or Phe or Leu]-Pro (SEQ ID NO: 203), wherein the Trp is either an N-terminal or internal residue, and the Pro is an internal residue. In one embodiment, the Trp is N-terminally preceded by X1 and/or X2 (i.e., X1-X2-Trp), wherein X1 is Leu or Val and X2 is Leu (SEQ ID NO: 204). In one embodiment, the invention provides an isolated polypeptide (e.g., a polypeptide as defined hereinbelow, which specifically includes peptide molecules) that binds specifically to Dvl PDZ, wherein said polypeptide comprises an N-terminal or internal region comprising, consisting, or consisting essentially of a binding motif comprising Trp-[Ile or Val]-Asp-Gly-Pro (SEQ ID NO: 168), wherein the Trp is either an N-terminal or internal residue, and the Pro is an internal residue. In one embodiment, the Trp is N-terminally preceded by X1 and/or X2 (i.e., X1-X2-Trp), wherein X1 is Glu and X2 is Thr, Val, Met, Arg, Ile or Gln (SEQ ID NO: 205).

In one aspect, the invention provides an isolated polypeptide that binds specifically to Dvl PDZ at a binding affinity of $IC_{50}$=1.5 uM or better. In one embodiment, the binding affinity is $IC_{50}$=1.2 uM or better. In one embodiment, the binding affinity is $IC_{50}$=1.0 uM or better. In one embodiment, the binding affinity is $IC_{50}$=0.8 uM or better. In one embodiment, the binding affinity is $IC_{50}$=0.6 uM or better. In one embodiment, the binding affinity is $IC_{50}$=0.4 uM or better. In one embodiment, the binding affinity is $IC_{50}$=0.2 uM or better. Binding affinities can be measured by any of a variety of methods known in the art. In one embodiment, the $IC_{50}$ binding affinity of polypeptides of the invention is determined as the mean concentration of a polypeptide that blocks about 50% of Dvl PDZ binding to an immobilized high affinity peptide ligand in a competition ELISA (e.g., as described Sidhu et al., *Methods Enzymol.* (2000), 328:333-363, and in the Examples below, wherein KWYGWL$_{COOH}$ (SEQ ID NO: 169) is utilized as a high affinity peptide ligand). In one embodiment, a polypeptide of the invention inhibits Dvl PDZ interaction with its binding parter, for example, Dvl PDZ interaction with its binding partner in a cell.

In one aspect, the invention provides a polypeptide that specifically binds Dvl PDZ, wherein said polypeptide comprises a C-terminal region comprising, consisting, or consisting essentially of a sequence with the following formula:

X1-G-X3-X4$_{COOH}$ wherein X1 is Y, L, F or I; X3 is W, M, F or Y; and X4 is F or L (SEQ ID NO: 184);

and wherein said sequence is not a naturally-occurring C-terminal sequence of a human protein. In one embodiment, the sequence comprises KWYGWL (SEQ ID NO: 169), where X1 is Y, X3 is W, and X4 is L. In one embodiment, said sequence is not a natural ligand for Dvl such as human ubiquitin protein ligase E3A (UBE3A). In one embodiment, X3 is Trp.

In one embodiment, the invention provides an isolated polypeptide that binds specifically to Dvl PDZ and comprises a carboxyl terminal region comprising, consisting, or consisting essentially of an amino acid sequence selected from the group consisting of the sequences of Table 1 and FIG. 1A for positions −5 to 0, or positions −6 to 0, wherein amino acid numbering is based on the C-terminus residue being in position 0.

In one aspect, the invention provides a polypeptide that specifically binds Dvl PDZ, wherein said polypeptide comprises a N-terminal or internal region comprising, consisting, or consisting essentially of a sequence with the following formula:

X1-G-X3-X4 wherein X1 is Y, C, L, F or S; X3 is W, M, F, I, V or Y; and X4 is I, V, M or L (SEQ ID NO: 185);

and wherein said sequence is not a naturally-occurring N-terminal or internal sequence of a human protein. In one embodiment, X1 is Y, X3 is W, and/or X4 is I or V (SEQ ID NO: 206). In one embodiment, X3 is Trp (SEQ ID NO: 207). In one embodiment, X1 is preceded by a D (SEQ ID NO: 208). In one embodiment, said sequence is not a natural ligand for Dvl such as human ubiquitin protein ligase E3A (UBE3A).

In one embodiment, the invention provides an isolated polypeptide that binds specifically to Dvl PDZ and comprises a N-terminal or internal region comprising, consisting, or consisting essentially of an amino acid sequence selected from the group consisting of the Type I and Type II sequences set forth in FIG. 1B for positions −9 to 0, −8 to 0, −7 to 0, −6 to 0, −5 to 0, wherein the numbers refer to the residue order as indicated in FIG. 1B. In one embodiment, said amino acid sequence further includes a tripeptide, GGG, C-terminal to the residue indicated for position 0 in FIG. 1B. In one embodiment, said amino acid sequence further includes DGGG (SEQ ID NO: 167) C-terminal to the residue indicated for position 0 in FIG. 1B.

In one aspect, the invention provides a polypeptide that specifically binds Dvl PDZ, wherein said polypeptide comprises a N-terminal or internal region comprising, consisting, or consisting essentially of a sequence with the following formula:

X1-X2-W—X3-D-X4-P wherein X1 and/or X2 is any naturally-occurring amino acid; X3 is S, T, A, W, D or I; and X4 is F, I, V, L or G (SEQ ID NO: 186);

and wherein said sequence is not a naturally-occurring N-terminal or internal sequence of a human protein. In one embodiment, X3 is S or T; and X4 is I, F or L (SEQ ID NO: 187). In one embodiment, X1 is L or V (SEQ ID NO: 188). In one embodiment, X2 is L (SEQ ID NO: 189). In one embodiment, the sequence comprises GEIVLWSDIPG (SEQ ID NO: 171), where X1 is V, X2 is L, X3 is S, and X4 is I. In one embodiment, said sequence is not a natural ligand for Dvl such as human ubiquitin protein ligase E3A (UBE3A).

In one aspect, the invention provides a polypeptide that specifically binds Dvl PDZ, wherein said polypeptide comprises a N-terminal or internal region comprising, consisting, or consisting essentially of a sequence with the following formula:

X1-X2-W—X3-D-X4-P wherein X1 and/or X2 is any naturally-occurring amino acid; X3 is I, G, V, K or W; and X4 is G, S, Y or W (SEQ ID NO: 190);

and wherein said sequence is not a naturally-occurring N-terminal or internal sequence of a human protein. In one embodiment, X3 is I or V; and X4 is G (SEQ ID NO: 191). In one embodiment, X1 is E (SEQ ID NO: 192). In one embodiment, X2 is T, V, M, R, I or Q (SEQ ID NO: 193). In one embodiment, said sequence is not a natural ligand for Dvl such as human ubiquitin protein ligase E3A (UBE3A).

In one embodiment, the invention provides an isolated polypeptide that binds specifically to Dvl PDZ and comprises a N-terminal or internal region comprising, consisting, or consisting essentially of an amino acid sequence selected from the group consisting of the Type III and Type IV sequences set forth in FIG. 1B for positions −6 to 0, −5 to 0, wherein the numbers refer to the residue order as indicated in FIG. 1B. In one embodiment, said amino acid sequence further includes one or more of the residues indicated for position 1, 2, 3, 4, 5, 6 and/or 7 in FIG. 1B (Type III and Type IV).

In one embodiment, polypeptides of the invention specifically exclude Dvl PDZ binder polypeptides that do not exhibit a desirable characteristic (such as binding affinity, e.g., wherein an example of a desirable characteristic is moderate to high affinity binding) of a binder peptide as disclosed herein (see, e.g., the Examples). For example, in one embodiment, a polypeptide of the invention does not comprise sequence YAKGFGML (SEQ ID NO: 170) wherein the C-terminal residue is carboxylated (i.e., if the sequence is in a polypeptide of the invention, the C-terminal residue L is not carboxylated or otherwise have a free carboxyl group.

In one aspect, the invention provides an isolated polypeptide comprising, consisting, or consisting essentially of an amino acid sequence that competes with one or more of the polypeptides described above for binding to Dvl PDZ.

In one aspect, the invention provides an isolated polypeptide that binds to the same epitope on Dvl PDZ as one or more of the polypeptides described above.

As shown herein, the PDZ domain of Dvl1, Dvl2 and Dvl3 share extensive sequence homology, and binder peptides described herein are capable of binding to at least one, at least two, or all three Dvl (1,2,3) proteins. In one embodiment, a polypeptide of the invention interacts with/binds to human Dvl 1, 2 and/or 3.

In some contexts, the nature of the end terminal residue in a binder polypeptide can affect the binding capability of a polypeptide. Accordingly, in one embodiment, an isolated Dvl PDZ-binding polypeptide of the invention comprises a carboxyl terminal amino acid residue which is carboxylated. In one embodiment, an isolated Dvl PDZ-binding polypeptide of the invention comprises a carboxyl terminal amino acid residue that is missing a free carboxyl group. In one embodiment, an isolated Dvl PDZ-binding polypeptide comprises a PDZ binding motif that does not comprise and/or require a free carboxyl group or residue.

In one aspect, a polypeptide of the invention comprises a Dvl PDZ binder polypeptide linked to a molecular entity that enhances polypeptide cell entry. In one embodiment, such molecular entity comprises an amino acid sequence tag, such as the sequence RQIKIWFQNRRMKWKK (SEQ ID NO: 172), which in one embodiment is acetylated on the N-terminus residue. For example, in one embodiment, a polypeptide of the invention comprises one of the following sequences:

```
(i)
RQIKIWFQNRRMKWKKKWYGWL,      (SEQ ID NO: 173)
or (ii)
RQIKIWFQNRRMKWKKGWKDYGWIDG,  (SEQ ID NO: 174)
or (iii)
RQIKIWFQNRRMKKGEIVLWSDIPG,   (SEQ ID NO: 175)
or (iv)
RQIKIWFQNRRMKWKKGSGNEVWIDGPG. (SEQ ID NO: 176)
```

In another aspect, the invention provides a polynucleotide encoding a polypeptide of the invention (as described herein).

In another aspect, the invention provides a host cell comprising a polynucleotide and/or polypeptide of the invention (as described herein).

In another aspect, the invention provides a composition comprising one or more of the polypeptides or polynucleotides of the invention (as described herein). In one embodiment, the composition comprises a carrier, which in some embodiments is pharmaceutically acceptable.

In another aspect, the invention provides a kit comprising one or more of the polypeptides or polynucleotides of the invention (as described herein). When one or more modulator molecules are provided, they can be provided separately or together, so long as they are in a formulation suitable for an intended use. In one embodiment, the kit comprises instructions for using the composition.

In one aspect, the invention provides Dvl modulator molecules comprising one or more of the polypeptides of the invention. These modulator molecules (including the polypeptides of the invention comprised therein) can be used in a variety of contexts, including but not limited to use as reference molecules in screening for Dvl PDZ modulators, use as diagnostic molecules, or use as therapeutic agents.

Modulator molecules of the invention can be used for diagnostic purposes. Accordingly, in one aspect, the invention provides a method of identifying dysregulation of Dvl PDZ-ligand interaction in a sample, said method comprising contacting the sample with a polypeptide of the invention, and comparing Dvl PDZ-ligand interaction in the presence and absence of the polypeptide of the invention whereby a detectable difference is indicative of the occurrence and/or amount of Dvl PDZ-ligand interaction in the sample. Dvl PDZ-ligand interaction can be measured in a variety of ways, for example by determining amount/extent of wnt signaling (e.g., by measuring one or more known downstream events from Dvl function in the wnt pathway).

In one aspect, the invention provides a method of identifying a compound capable of modulating Dvl PDZ-ligand interaction, said method comprising contacting a sample comprising:

(i) Dvl PDZ, a functional fragment and/or equivalent thereof, (ii) one or more of the polypeptides of the invention as a reference; and (iii) a candidate compound;

and determining the amount of Dvl PDZ-reference interaction in the presence of the candidate compound;

whereby a change in the amount of Dvl PDZ-reference interaction in the presence of the candidate compound compared to the amount in the absence of the compound indicates that the candidate compound is a compound capable of modulating Dvl PDZ-ligand interaction. In one embodiment, the compound is a small molecule (such as organic molecules, peptides) or antibody (including fragments thereof).

In one aspect, the invention provides a method of rationally designing a modulator of Dvl PDZ-ligand interaction comprising designing the modulator to comprise or mimic the function of a C-terminal peptide comprising a sequence with Gly at position −2, Trp or Tyr at position −1, Phe or Leu at position 0, and a hydrophobic or aromatic residue at position −3 (SEQ ID NO: 194), wherein amino acid numbering is based on the C-terminus residue being in position 0, wherein the modulator is capable of specifically binding to Dvl PDZ.

In one aspect, the invention provides a method of rationally designing a modulator of Dvl PDZ-ligand interaction comprising designing the modulator to comprise or mimic the function of a N-terminal or internal peptide comprising the sequence Gly-Trp-[Ile or Val]-X1-X2-X3-X4 (SEQ ID NO: 196) or Tyr-Gly-Trp-[Ile or Val]-X1-X2-X3-X4 (SEQ ID NO: 197), wherein Gly is either an N-terminal or internal residue, respectively, and X1, X2, X3 and/or X4 are internal residues. In one embodiment, X1-X2-X3 is G-G-G (SEQ ID NO: 198; SEQ ID NO: 199). In one embodiment, X1-X2-X3-X4 is D-G-G-G (SEQ ID NO: 167; SEQ ID NO: 200; SEQ ID NO: 201). In one embodiment, the Tyr is preceded N-terminally by Asp (SEQ ID NO: 202). If any of these embodiments, the modulator is designed to be capable of specifically binding to Dvl PDZ.

In one aspect, the invention provides a method of rationally designing a modulator of Dvl PDZ-ligand interaction comprising designing the modulator to comprise or mimic the function of a N-terminal or internal peptide comprising the sequence Trp-[Ser or Thr]-Asp-[Ile or Phe or Leu]-Pro (SEQ ID NO: 203), wherein the Trp is either an N-terminal or internal residue, and the Pro is an internal residue. In one embodiment, the Trp in said sequence is N-terminally preceded by X1 and/or X2 (i.e., X1-X2-Trp), wherein X1 is Leu or Val and X2 is Leu (SEQ ID NO: 204). In any of these embodiments, the modulator is designed to be capable of specifically binding to Dvl PDZ.

In one aspect, the invention provides a method of rationally designing a modulator of Dvl PDZ-ligand interaction comprising designing the modulator to comprise or mimic the function of a N-terminal or internal peptide comprising the sequence Trp-[Ile or Val]-Asp-Gly-Pro (SEQ ID NO: 168), wherein the Trp is either an N-terminal or internal residue, and the Pro is an internal residue. In one embodiment, the Trp in said sequence is N-terminally preceded by X1 and/or X2 (i.e., X1-X2-Trp), wherein X1 is Glu and X2 is Thr, Val, Met, Arg, Ile or Gln (SEQ ID NO: 205). In any of these embodiments, the modulator is designed to be capable of specifically binding to Dvl PDZ.

In one aspect, the invention provides a method of screening for an agent that modulates Dvl PDZ-ligand interaction, wherein the method comprises the steps of:

(a) providing a candidate agent and contacting said agent with a reaction mixture comprising Dvl PDZ and a known binding parter of said Dvl PDZ (e.g., a polypeptide of the invention), wherein said mixture is a cell mixture or a cell-free mixture, and the contacting occurs under conditions suitable for Dvl PDZ-binding partner interaction;

(b) determining amount of Dvl PDZ-binding partner interaction in the presence and absence of the agent;

whereby a difference between the amount of interaction as determined in (b) in the presence and absence of the agent indicates that the agent is a modulator of Dvl PDZ-ligand interaction. In one embodiment, the candidate agent is a small molecule (such as organic molecules, peptides) or antibody (including fragments thereof).

In one embodiment of the foregoing methods, where appropriate, the PDZ ligand in a sample or reaction mixture is a naturally-occurring ligand (e.g., an endogenous Dvl PDZ ligand).

Polypeptides of the invention are useful for a variety of purposes and in a variety of settings in which modulation of wnt signaling via the Dvl protein is desired. For example, a polypeptide of the invention can be used to inhibit Dvl-mediated Wnt signaling, for example, in a cell, to alter the course of any disorder associated with dysregulation of Wnt signaling.

In one aspect, the invention provides a method of treating a pathological condition associated with dysregulation of Dvl or wnt protein activity comprising administering to a subject an effective amount of a Dvl PDZ-ligand modulator, wherein the modulator is capable of modulating interaction between Dvl PDZ and a polypeptide of the invention. In one embodiment of a method of the invention, the modulator inhibits interaction between Dvl PDZ and its binding partner (e.g., an endogenous binding partner). In one embodiment, said Dvl-PDZ ligand modulator comprises one or more of the polypeptides of the invention as described herein. In one embodiment, the pathological condition is cancer. In one embodiment, the pathological condition is a hyperproliferative disorder. In one embodiment, the pathological condition is associated with dysregulation of canonical wnt signaling pathway. In one embodiment, the Dvl is human Dvl 1, 2 and/or 3.

BRIEF DESCRIPTION OF THE DRAWINGS

FIG. 1. Dvl2 PDZ binding peptides selected from phage-displayed libraries (SEQ ID NOS 5-166, respectively, in order of appearance).

The sequences were selected from libraries fused to the C-terminus (A) or (B) N-terminus of p8 phage coat protein. Positions in the peptide ligand, from the C-terminus to the N-terminus, are designated 0, −1, etc.

Figure 2:
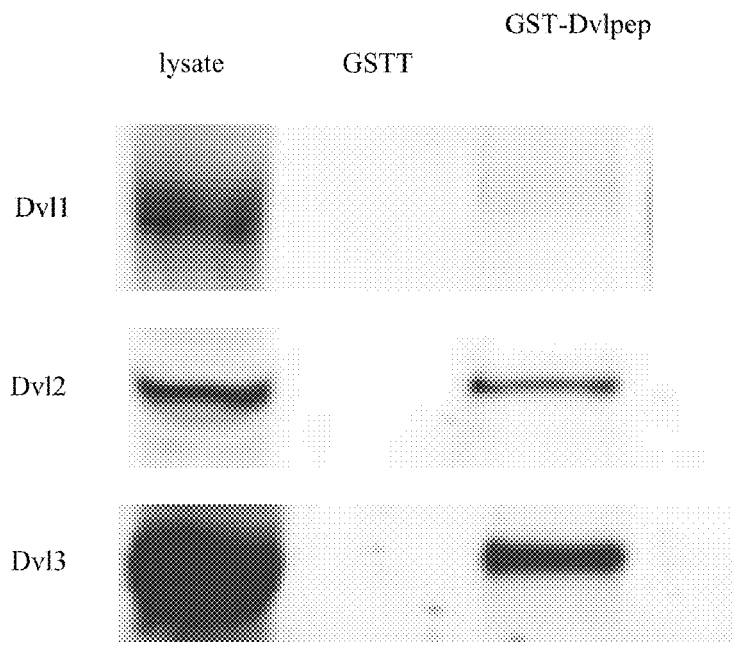

FIG. 2. (A) Sequence alignment of the PDZ domains of human Dvl-1, -2 and -3 (SEQ ID NOS 1-4, respectively, in order of appearance).

Identities are highlighted in dark shade and similarities are highlighted in grey shade.

FIG. 2. (B) Dvl PDZ peptide ligand can pull down all 3 endogenous Dvl (i.e., 1, 2, 3).

Cell lysate of HEK293S cell was prepared and the whole protein concentration was normalized to 1 mg/ml. GST or GST-DVLpep fusion protein was bound to glutathione Sepharose-4B. Beads carrying protein (2-10 µg) were incubated with cell extract of HEK293S cells overnight at 4° C. The beads were washed with washing buffer (PBS, 0.5% BSA, 0.1% Tween 20) for 10 times and resuspended in SDS sample buffer, incubated at 90° C. for 10 min and the supernatant was subjected to SDS-PAGE. The crude cell extract was also subjected to the same SDS-PAGE. Dvl proteins were blotted by anti-Dvl1, anti-Dvl2, and anti-Dvl3.

FIG. 3. (A) Dvl PDZ peptide ligands, DVLp_C and Dvlp_N3, significantly blocked the Wnt-stimulated increase in β-catenin signaling in HEK293S cells.

HEK293S cells were transfected with the reporter plasmid pTOPGLOW combined with pRL reporter. Cell extract was prepared and the luciferase activity was measured. The relative luciferase unit (RLU) is TopGlow luciferase activity divided by Renila luciferase activity. The fold of activation is the RLU ratio between the Wnt3a-stimulated and non-stimulated cells. Cells were treated with either 10 µM (light bar) or 20 µM (dark bar) peptide ligands.

FIGS. 3 (B) and (C). The inhibition of Wnt-stimulated increase in β-catenin signaling in HEK293S cells by Dvlp_C (B) and Dvlp_N3(C) was dose-dependent.

The data was obtained by measurements in two independent experiments.

FIGS. 3 (D) and (E). Dvl PDZ peptide ligands, DVLp_C (D) and Dvlp_N3(E), reduced the Wnt-stimulated increase in β-catenin protein level.

HEK293S cells were treated with 20 µM DVLp and PEN for 24 hours. Cell lysate was prepared and subjected to SDS-PAGE. β-catenin was blotted by poly-clonal anti-β-catenin (Genentech, Inc., South San Francisco).

Figure 4:
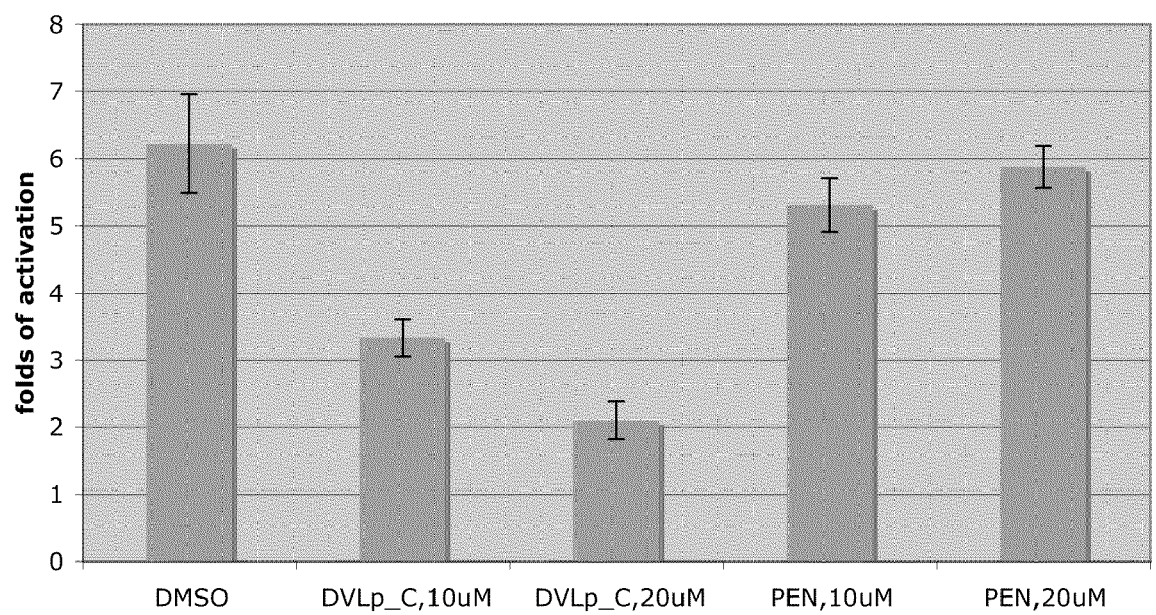

FIG. 4. Dvl PDZ peptide ligand, DVLp_C, blocked the Wnt-stimulated increase in β-catenin signaling in NCI-H1703 cells.

NCI-H1703 cells were transfected with the reporter plasmid pTOPGLOW combined with pRL reporter. Cell extract was prepared and the luciferase activity was measured. The relative luciferase unit is TopGlow luciferase activity divided by Renila luciferase activity. The fold of activation is the RLU ratio between the Wnt3a-stimulated or non-stimulated cells.

Figure 5:
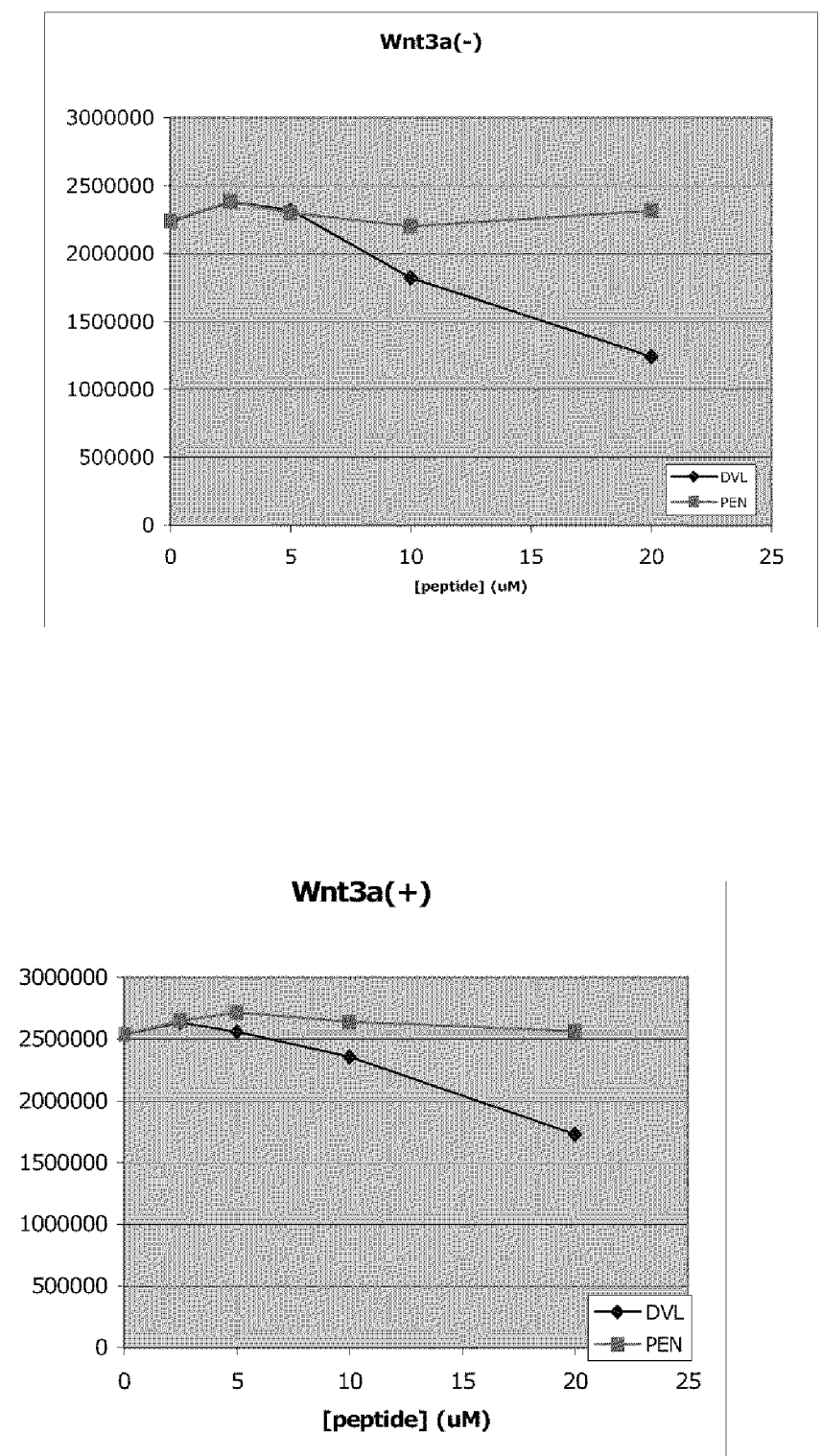

FIG. 5 (A) Dvl PDZ ligand treatment reduced viability of NCI-H1703 cells.

Cells were seeded in black wall 96-well plate in triplicate and treated with various doses of peptide on Day 0 and were incubated at 37° C. in a humid incubator with 5% $CO_2$. After 72 hours, Alamar Blue assay was performed.

FIG. 5 (B) Dvl PDZ ligand treatment suppresses the cell growth of NCI-H1703 cells.

Cells were seeded in black wall 96-well plate in triplicate and treated with 10 µM peptide or DMSO on Day 0, and the cell viability was measured by Alamar Blue assay after 24, 48 and 72 hours.

MODES FOR CARRYING OUT THE INVENTION

The invention provides molecules, and methods for identifying and using molecules, capable of modulating binding interactions between the PDZ domain of the Dvl proteins and their cellular binding partner(s). In one aspect, these molecules are generated by a combinatorial approach that results in the identification of peptide binders capable of binding to Dvl PDZ at various affinities. The identification of these binder molecules, and the structural dynamics of the binding interaction between Dvl PDZ and these binder polypeptides, as extensively described herein, further provide a means to identify other modulators capable of interacting with Dvl PDZ. In light of the importance of Dvl in various cellular and physiological processes, these modulators would be of significant utility, such as in prophylactic, therapeutic and/or diagnostic settings.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988).

Oligonucleotides, polynucleotides, peptides, polypeptides and small molecules employed or described in the present invention can be generated using standard techniques known in the art.

Definitions

"Control sequences", as used herein, are DNA sequences that enable the expression of an operably-linked coding sequence in a particular host organism. Prokaryotic control sequences include promoters, operator sequences, and ribosome binding sites. Eukaryotic control sequences include promoters, polyadenylation signals, and enhancers.

Nucleic acid is "operably-linked" when it is placed into a functional relationship with another nucleic acid sequence. For example, a promoter or enhancer is operably-linked to a coding sequence if it affects the transcription of the sequence, or a ribosome-binding site is operably-linked to a coding sequence if positioned to facilitate translation. Generally, "operably-linked" means that the DNA sequences being linked are contiguous, and, in the case of a secretory leader, contiguous and in reading phase. However, enhancers do not have to be contiguous.

An "active" polypeptide, or fragments thereof, retains a biological activity of native or naturally-occurring counterpart of the active polypeptide. Biological activity refers to a function mediated by the native or naturally-occurring counterpart of the active polypeptide. For example, binding or protein-protein interaction constitutes a biological activity.

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein).

The light chains of antibodies from any vertebrate species can be assigned to one of two clearly distinct types, called kappa ($\kappa$) and lambda ($\lambda$), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG-1, IgG-2, IgA-1, IgA-2, and etc. The heavy chain constant domains that correspond to the different classes of immunoglobulins are called $\alpha$, $\beta$, $\epsilon$, $\gamma$, and $\mu$, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

An antibody can be chimeric, human, humanized and/or affinity matured.

"Antibody fragments" comprise only a portion of an intact antibody, wherein the portion preferably retains at least one, preferably most or all, of the functions normally associated with that portion when present in an intact antibody.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

An "epitope tagged" polypeptide refers to a chimeric polypeptide fused to a "tag polypeptide". Such tags provide epitopes against which Abs can be made or are available, but do not substantially interfere with polypeptide activity. To reduce anti-tag antibody reactivity with endogenous epitopes, the tag polypeptide is usually unique. Suitable tag polypeptides generally have at least six amino acid residues, usually between about 8 and 50 amino acid residues, preferably between 8 and 20 amino acid residues. Examples of epitope tag sequences include HA from Influenza A virus, GD, and c-myc, poly-His and FLAG.

"Polynucleotide," or "nucleic acid," as used interchangeably herein, refer to polymers of nucleotides of any length, and include, but are not limited to, DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR.sub.2 ("amidate"), P(O)R, P(O)OR', CO or CH.sub.2 ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "peptide" generally refers to a contiguous and relatively short sequence of amino acids linked by peptidyl bonds. Typically, but not necessarily, a peptide has a length of about 2 to 50 amino acids, 4-40 amino acids or 10-30 amino acids. Although the term "polypeptide" generally refers to longer forms of a peptide, the two terms can be and are used interchangeably in some contexts herein.

A "region" of a polypeptide is a contiguous sequence of 2 or more amino acids. In other embodiments, a region is at least about any of 3, 5, 10, 15 contiguous amino acids.

"C-terminal region", "C-terminal sequence", and variations thereof, as used herein, refer to an amino acid sequence that is located at or in close proximity to the C-terminal (generally 3') end of a polypeptide. Generally, the sequence includes an amino acid that has a free carboxyl group. In one embodiment, a C-terminal region or sequence refers to a region of a polypeptide that includes the about 1-15 residues located closest to the C terminus of the polypeptide.

"N-terminal region", "N-terminal sequence", and variations thereof, as used herein, refer to an amino acid sequence that is located at or in close proximity to the N-terminal (generally 5') end of a polypeptide. Generally, the sequence includes an amino acid that has a free amino group. In one embodiment, a N-terminal region or sequence refers to a region of a polypeptide that includes the about 1-15 residues located closest to the N terminus of the polypeptide.

"Internal region", "internal sequence", and variations thereof, as used herein, refer to an amino acid sequence that is located within a polypeptide and is flanked on both its N- and C-termini by one or more amino acids that are not part of the sequence. Generally, the sequence does not include an amino acid with either a free carboxyl or amino group. In one embodiment, an internal region or sequence refers to a region of a polypeptide that includes the about 1-15 residues located within a polypeptide, wherein the region does not include either the C-terminal or N-terminal amino acid.

A "PDZ domain", which is also known as DHR (DLG homology region) or the GLGF repeat, is a protein domain originally described as conserved structural elements in the 95 kDa post-synaptic density protein (PSD-95), the *Drosophila* tumor suppressor discs-large, and the tight junction protein zonula occludens-1 (ZO-1), which are found in a large and diverse set of proteins, including the Dvl proteins. PDZ domains generally bind to short carboxyl-terminal peptide sequences located on the carboxyl-terminal end of interacting proteins. Usually, PDZ domains comprise two α helixes and six β sheets.

"Dvl PDZ domain", "Dvl PDZ", and variations thereof, refer to part or all of the sequences of SEQ ID NO:1, 2 and 3 (FIG. 2), which is directly or indirectly involved in cellular Dvl PDZ-ligand interactions. "Dvl1 PDZ" refers to the PDZ domain of Dvl1; "Dvl2 PDZ" refers to the PDZ domain of Dvl2; and "Dvl3 PDZ" refers to the PDZ domain of Dvl3.

The term "Disheveled" or "Dvl" refers to a member of a family of Disheveled proteins, the full-length sequences of which typically possess three conserved domains, a DIX domain, present in the Wnt antagonizing protein Axin; a PDC domain involved in protein-protein interactions, and a DEP domain found in rpoteins that regulate Rho GTPases. Dvl proteins include, for example, Dvl-1, Dvl-2, and Dvl-3. Nucleic acid and protein Dvl sequence are known from a variety of species, including mouse and human. Exemplary human Dvl-1, Dvl-2, and Dvl-3 protein sequences are available under reference sequences NP_004412, NP_004413, and NP_004414, respectively. See also, WO2006/007542.

A "ligand" refers to a naturally-occurring or synthetic molecule or moiety that is capable of a binding interaction with a specific site on a protein or other molecule; a Dvl PDZ domain ligand is a molecule or moiety that specifically interacts with Dvl PDZ domain. Examples of ligands include proteins, peptides, and small organic and inorganic molecules.

A "fusion protein" refers to a polypeptide having two portions covalently linked together, where each of the portions is derived from different proteins. The two portions may be linked directly by a single peptide bond or through a peptide linker containing one or more amino acid residues. Generally, the two portions and the linker will be in reading frame with each other and are produced using recombinant techniques.

A "disorder" or "pathological condition" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors or cancers; non-leukemias and lymphoid malignancies; neuronal, glial, astrocytal, hypothalamic and other glandular, macrophagal, epithelial, stromal and blastocoelic disorders; and inflammatory, immunologic, neurodegenerative disorders, angiogenesis-related disorders and disorders related to mitochondrial or metabolic defects.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, modulatory compounds of the invention are used to delay development of a disease or disorder.

An "effective amount" refers to an amount effective, at dosages and for periods of time necessary, to achieve the desired therapeutic or prophylactic result. A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

Modulators of Dvl PDZ-ligand Interaction

The invention provides modulators, and methods for identifying modulators of Dvl PDZ-ligand interaction in vivo. One way to modulate the interaction between Dvl PDZ domain and its ligand is to inhibit the interaction. Any molecule that disrupts Dvl PDZ-ligand interaction can be a candidate inhibitor. Screening techniques well known to those skilled in the art can identify these molecules. Examples of inhibitors include: (1) small organic and inorganic compounds, (2) small peptides, (3) antibodies and derivatives, (4) peptides closely related to PDZ-domain ligand (5) nucleic acid aptamers. "Dvl PDZ-domain-ligand interaction inhibitor" includes any molecule that partially or fully blocks, inhibits, or neutralizes the interaction between Dvl PDZ domain and its ligand. Molecules that may act as such inhibitors include peptides that bind Dvl PDZ domain, such as the peptide binders listed in Table I (for example and in particular peptides KWYGWL (SEQ ID NO: 169); KWYGWF (SEQ ID NO: 177); WKWYGWL (SEQ ID NO: 178); WKWYGWF (SEQ ID NO: 179)), Table II (for example and in particular peptides GWKDYGWIDG (SEQ ID NO: 180); GEIVLWSDIPG (SEQ ID NO: 171)), the peptide binders listed in FIG. 1 (SEQ ID NOs: 5-166); antibodies (Ab's) or antibody fragments, and other small organic or inorganic molecules.

Small Molecule Dvl PDZ Modulators

Small molecules can be useful modulators of Dvl PDZ-ligand interaction. Small molecules that inhibit this interaction are potentially useful inhibitors. Examples of small molecule modulators include small peptides, peptide-like molecules, soluble, and synthetic, non-peptidyl organic or inorganic compounds. A "small molecule" refers to a composition that has a molecular weight of for example less than about 5 kD, less than about 4 kD, and less than 0.6 kD. Small molecules can be nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays. Examples of methods for the synthesis of molecular libraries have been described (Carell et al., *Angewandte Chemie International Edition.* 33:2059-2061 (1994); Carell et al., *Angewandte Chemie International Edition.* 33:2061-2064 (1994); Cho et al., *Science.* 261:1303-5 (1993); DeWitt et al., *Proc Natl Acad Sci USA.* 90:6909-13 (1993); Gallop et al., *J Med Chem.* 37:1233-51 (1994); Zuckermann et al., *J Med Chem.* 37:2678-85 (1994).

Libraries of compounds may be presented in solution (Houghten et al., *Biotechniques.* 13:412-21 (1992)) or on beads (Lam et al., *Nature.* 354:82-84 (1991)), on chips (Fodor et al., *Nature.* 364:555-6 (1993)), bacteria, spores (Ladner et al., U.S. Pat. No. 5,223,409, 1993), plasmids (Cull et al., *Proc Natl Acad Sci USA.* 89:1865-9 (1992)) or on phage (Cwirla et al., *Proc Natl Acad Sci USA.* 87:6378-82 (1990); Devlin et al., *Science.* 249:404-6 (1990); Felici et al., *J Mol Biol.* 222:301-10 (1991); Ladner et al., U.S. Pat. No. 5,223,409, 1993; Scott and Smith, *Science.* 249:386-90 (1990)). A cell-free assay comprises contacting Dvl PDZ with a known binder molecule (such as one or more of the binder polypeptides of the invention described herein) to form an assay mixture, contacting the assay mixture with a test compound, and determining the ability of the test compound to interact with Dvl PDZ or the binder molecule, where determining the ability of the test compound to interact with Dvl PDZ or the binder molecule comprises determining whether a detectable characteristic of Dvl PDZ/binder complex is modulated. For example, the binding interaction of Dvl PDZ and the binder molecule, as determined by the amount of complex that is formed, can be indicative of whether the test compound is able to modulate the interaction between Dvl PDZ and the binder molecule. Amount of complex can be assessed by methods known in the art, some of which are described herein, for example ELISA (including competitive binding ELISA), yeast two-hybrid and proximity (e.g., fluorescent resonance energy transfer, enzyme-substrate) assays.

Polypeptide/Peptide and Antibody Dvl PDZ Modulators

One aspect of the invention pertains to isolated peptide/polypeptide modulators of the interaction between Dvl PDZ and its cellular and/or physiological binding partner(s). The binder polypeptides of the invention described herein, and polypeptide modulators obtained by methods described herein are also suitable for use as immunogens to raise antibody modulators of this interaction. In one embodiment, modulators (such as peptides and antibodies) can be isolated from cells or tissue sources by an appropriate purification scheme using standard protein purification techniques. In another embodiment, the modulators are produced by recombinant DNA techniques. Alternative to recombinant expression, modulators can be synthesized chemically using standard peptide synthesis techniques.

Dvl PDZ binder molecules of the invention include those described in Table I, II, and FIG. 1. The invention also provides a mutant or variant protein any of which residues may be changed from the corresponding residues of these peptides, while still encoding a peptide that maintains modulatory activity. In one embodiment, a variant of a binder peptide/polypeptide/ligand has at least 50%, 60%, 70%, 80%, 90%, 95%, 98%, 99% amino acid sequence identity with the sequence of a reference binder peptide/polypeptide/ligand. In general, the variant exhibits substantially the same or greater binding affinity than the reference binder peptide/polypeptide/ligand, e.g., at least 0.75×, 0.8×, 0.9×, 1.0×, 1.25× or 1.5× the binding affinity of the reference binder peptide/polypeptide/ligand, based on an art-accepted binding assay quantitation unit/metric.

In general, variants of the invention include variants in which residues at a particular position in the sequence have been substituted by other amino acids, and further includes the possibility of inserting an additional residue or residues between two residues of the parent protein/peptide as well as the possibility of deleting one or more residues from the parent sequence or adding one or more residues to the parent sequence. Any amino acid substitution, insertion, or deletion is encompassed by the invention. In favorable circumstances, the substitution is a conservative substitution as described herein.

"Percent (%) amino acid sequence identity" is defined as the percentage of amino acid residues that are identical with amino acid residues in a reference (parent) polypeptide sequence when the two sequences are aligned. To determine % amino acid identity, sequences are aligned and if necessary, gaps are introduced to achieve the maximum % sequence identity; conservative substitutions are not considered as part of the sequence identity. Amino acid sequence, alignment procedures to determine percent identity are well known to those of skill in the art. Often publicly available computer software such as BLAST, BLAST2, ALIGN2 or Megalign (DNASTAR) software is used to align peptide sequences. Those skilled in the art can determine appropriate parameters for measuring alignment, including any algorithms needed to achieve maximal alignment over the full length of the sequences being compared.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

$$\text{\% amino acid sequence identity} = X/Y \cdot 100$$

where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A.

An "isolated" or "purified" peptide, polypeptide, protein or biologically active fragment is separated and/or recovered from a component of its natural environment. Contaminant components include materials that would typically interfere with diagnostic or therapeutic uses for the polypeptide, and may include enzymes, hormones, and other proteinaceous or non-proteinaceous materials. Preparations having preferably less than 30% by dry weight of non-desired contaminating material (contaminants), preferably less than 20%, 10%, and preferably less than 5% contaminants are considered to be substantially isolated. An isolated, recombinantly-produced peptide/polypeptide or biologically active portion thereof is preferably substantially free of culture medium, i.e., culture medium represents preferably less than 20%, preferably less than about 10%, and preferably less than about 5% of the volume of a peptide/polypeptide preparation. Examples of contaminants include cell debris, culture media, and substances used and produced during in vitro synthesis of the peptide/polypeptide.

Conservative substitutions of peptides/polypeptides are shown in Table A under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr; cys | cys |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the peptide/polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Variants of antibody modulators of Dvl PDZ-ligand interaction can also be made based on information known in the art, without substantially affecting the activity of antibody. For example, antibody variants can have at least one amino acid residue in the antibody molecule replaced by a different residue. For antibodies, the sites of greatest interest for substitutional mutagenesis generally include the hypervariable regions, but framework region (FR) alterations are also contemplated.

For antibodies, one type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In one embodiment, the Fc region variant may display altered neonatal Fc receptor (FcRn) binding affinity. Such variant Fc regions may comprise an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Fc region variants with reduced binding to an FcRn may comprise an amino acid modification at any one or more of amino acid positions 252, 253, 254, 255, 288, 309, 386, 388, 400, 415, 433, 435, 436, 439 or 447 of the Fc region, wherein the numbering of the residues in the Fc region is that of the EU index as in Kabat. The above-mentioned Fc region variants may, alternatively, display increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc region, wherein the numbering of the residues in the Fc region is that of the EU index as in Kabat.

The Fc region variant with reduced binding to an FcγR may comprise an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region, wherein the numbering of the residues in the Fc region is that of the EU index as in Kabat.

For example, the Fc region variant may display reduced binding to an FcγRI and comprise an amino acid modification at any one or more of amino acid positions 238, 265, 269, 270, 327 or 329 of the Fc region, wherein the numbering of the residues in the Fc region is that of the EU index as in Kabat.

The Fc region variant may display reduced binding to an FcγRII and comprise an amino acid modification at any one or more of amino acid positions 238, 265, 269, 270, 292, 294, 295, 298, 303, 324, 327, 329, 333, 335, 338, 373, 376, 414, 416, 419, 435, 438 or 439 of the Fc region, wherein the numbering of the residues in the Fc region is that of the EU index as in Kabat.

The Fc region variant of interest may display reduced binding to an FcγRIII and comprise an amino acid modification at one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region, wherein the numbering of the residues in the Fc region is that of the EU index as in Kabat.

Fc region variants with altered (i.e. improved or diminished) Clq binding and/or Complement Dependent Cytotoxicity (CDC) are described in WO99/51642. Such variants may comprise an amino acid substitution at one or more of amino acid positions 270, 322, 326, 327, 329, 331, 333 or 334 of the Fc region. See, also, Duncan & Winter *Nature* 322:738-40 (1988); U.S. Pat. No. 5,648,260; U.S. Pat. No. 5,624,821; and WO94/29351 concerning Fc region variants.

Vector Construction

Polynucleotide sequences encoding the peptide and polypeptides described herein can be obtained using standard synthetic and/or recombinant techniques. Desired polynucleotide sequences may be isolated and sequenced from appropriate source cells. Source cells for antibodies would include antibody producing cells such as hybridoma cells. Alternatively, polynucleotides can be synthesized using nucleotide synthesizer or PCR techniques. Once obtained, sequences encoding the peptide or polypeptide are inserted into a recombinant vector capable of replicating and expressing heterologous polynucleotides in a host cell. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication (in particular when the vector is inserted into a prokaryotic cell), a selection marker gene, a promoter, a ribosome binding site (RBS), a signal sequence, the heterologous nucleic acid insert and a transcription termination sequence.

In general, plasmid vectors containing replicon and control sequences which are derived from a species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as *E. coli* LE392.

Either constitutive or inducible promoters can be used in the present invention, in accordance with the needs of a particular situation, which can be ascertained by one skilled in the art. A large number of promoters recognized by a variety of potential host cells are well known. The selected promoter can be operably linked to cistron DNA encoding a polypeptide described herein by removing the promoter from the source DNA via restriction enzyme digestion and inserting the isolated promoter sequence into the vector of choice. Both the native promoter sequence and many heterologous promoters may be used to direct amplification and/or expression of the target genes. However, heterologous promoters are preferred, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In some embodiments, each cistron within a recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP.

Prokaryotic host cells suitable for expressing polypeptides include *Archaebacteria* and *Eubacteria*, such as Gram-negative or Gram-positive organisms. Examples of useful bacteria include *Escherichia* (e.g., *E. coli*), *Bacilli* (e.g., *B. subtilis*), *Enterobacteria*, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. Preferably, gram-negative cells are used. Preferably the host cell should secrete minimal amounts of proteolytic enzymes, and additional protease inhibitors may desirably be incorporated in the cell culture.

Peptide or Polypeptide Production

Host cells are transformed or transfected with the above-described expression vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In preferred embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector, protein expression is induced under conditions suitable for the activation of the promoter. For example, if a PhoA promoter is used for controlling transcription, the transformed host cells may be cultured in a phosphate-limiting medium for induction. A variety of other inducers may be used, according to the vector construct employed, as is known in the art.

Polypeptides described herein expressed in a microorganism may be secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therefrom. Cells may be removed from the culture and the culture supernatant being filtered and concentrated for further purification of the proteins produced. The expressed polypeptides can be further isolated and identified using commonly known methods such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins, ligand affinity using a suitable antigen immobilized on a matrix and Western blot assay.

Besides prokaryotic host cells, eukaryotic host cell systems are also well established in the art. Suitable hosts include mammalian cell lines such as CHO, and insect cells such as those described below.

Polypeptide/Peptide Purification

Polypeptides/peptides that are produced may be purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

Identification and Characterization of Dvl PDZ Modulators—General Approach

Candidate Dvl PDZ modulators, e.g. binding peptides, can be identified by any number of methods known in the art. The modulatory characteristics of modulators can be assessed by determining the ability of the modulators to modulate the interaction between Dvl PDZ and its binding partners (such as binding polypeptides of the invention). One of the important characteristics is binding affinity. The binding characteristics of candidate modulators (e.g. peptides) of interest can be assessed in any of a number of ways known in the art.

An initial step in the process can include generating one or more candidate peptides comprising sequences of interest, which are then displayed under conditions suitable to determine their Dvl PDZ domain binding characteristics. For example, candidate peptides can be displayed as carboxyl-terminal (C-terminal) display libraries of peptides on the surface of a phage or phagemid, for example a filamentous phage(mid) using protein fusions with a coat protein such as p3 or p8. C-terminal display is known in the art. See, e.g., Jespers et al., *Biotechnology* (NY). 13:378-82 and WO 00/06717. These methods may be used to prepare the fusion genes, fusion proteins, vectors, recombinant phage particles, host cells and libraries thereof of the invention. As described herein, in some embodiments, it may be useful to display candidate peptides as amino-terminal (N-terminal) display libraries of peptides on the surface of a phage or phagemid. Methods of N-terminal phage(mid) display include those described herein, and those that are well known in the art, e.g., as described in U.S. Pat. No. 5,750,373 (and references cited therein). Methods of characterizing binder molecules obtained by these methods are also known in the art, including those disclosed in the references cited above (Jespers et al., WO 00/06717 & U.S. Pat. No. 5,750,373) and as described herein.

(i) Isolation of Binding Phage to Dvl PDZ

A phage display library with the displayed candidate Dvl PDZ binding peptides is contacted with Dvl PDZ domain proteins or fusion proteins in vitro to determine those members of the library that bind to a Dvl PDZ domain target. Any method known to the skilled artisan may be used to assay for in vitro protein binding. For example, 1, 2, 3 or 4 rounds or more of binding selection may be performed, after which individual phage are isolated and, optionally, analyzed in a phage ELISA. Binding affinities of peptide-displaying phage particles to immobilized PDZ target proteins may be determined using a phage ELISA (Barrett et al., *Anal Biochem.* 204:357-64 (1992)).

In a situation wherein the candidate is being assessed for the ability to compete with a known Dvl PDZ binder for binding to Dvl PDZ, the appropriate binding competition conditions are provided. For example, in one embodiment, screening/selection/biopanning can be performed in the presence of one or more concentrations of the known Dvl PDZ binder. In another embodiment, candidate binders isolated from the library can be subsequently assessed in a competitive ELISA assay in the presence of the known Dvl PDZ binder.

(ii) Preparation of Dvl PDZ Domains

Dvl PDZ domains may be produced conveniently as protein fragments containing the domain or as fusion polypeptides using conventional synthetic or recombinant techniques. Fusion polypeptides are useful in phage(mid) display wherein Dvl PDZ domain is the target antigen, in expression studies, cell-localization, bioassays, ELISAs (including binding competition assays), etc. An Dvl PDZ domain "chimeric protein" or "fusion protein" comprises Dvl PDZ domain fused to a non-PDZ domain polypeptide. A non-PDZ domain polypeptide is not substantially homologous to the PDZ domain. An Dvl PDZ domain fusion protein may include any portion to the entire PDZ domain, including any number of the biologically active portions. The fusion protein can then be purified according to known methods using affinity chromatography and a capture reagent that binds to the non-PDZ domain polypeptide. Dvl PDZ domain may be fused to an affinity sequence, e.g. the C-terminus of the GST (glutathione S-transferase) sequences. Such fusion proteins facilitate the purification of the recombinant Dvl PDZ domain using, e.g., glutathione bound to a solid support and/or attachment to solid support (e.g., a matrix for peptide screening/selection/biopanning). Additional exemplary fusions are presented in Table B, including some common uses for such fusions.

Fusion proteins can be easily created using recombinant methods. A nucleic acid encoding Dvl PDZ domain (or portion thereof) can be fused in-frame with a non-PDZ domain encoding nucleic acid, at the PDZ domain N-terminus, C-terminus or internally. Fusion genes may also be synthesized by conventional techniques, including automated DNA synthesizers. PCR amplification using anchor primers that give rise to complementary overhangs between two consecutive gene fragments that can subsequently be annealed and reamplified to generate a chimeric gene sequence (Ausubel et al., Current protocols in molecular biology. John Wiley & Sons, New York 1987) is also useful. Many vectors are commercially available that facilitate sub-cloning the Dvl PDZ domain in-frame to a fusion protein.

TABLE B

Useful non-PDZ domain fusion polypeptides

| Fusion partner | in vitro | in vivo |
|---|---|---|
| Human growth hormone (hGH) | Radioimmuno-assay | none |
| β-glucuronidase (GUS) | Colorimetric, fluorescent, or chemi-luminescent | colorimetric (histo-chemical staining with X-gluc) |
| Green fluorescent protein (GFP) and related molecules (RFP, BFP, YFP domain, etc.) | Fluorescent | fluorescent |
| Luciferase (firefly) | bioluminsecent | Bioluminescent |
| Chloramphenicoal acetyltransferase (CAT) | Chromatography, differential extraction, fluorescent, or immunoassay | none |
| β-galacto-sidase | colorimetric, fluorescence, chemi-luminscence | colorimetric (histochemical staining with X-gal), bio-luminescent in live cells |
| Secrete alkaline phosphatase (SEAP) | colorimetric, bioluminescent, chemi-luminescent | none |
| Tat from HIV | Mediates delivery into cytoplasm and nuclei | Mediates delivery into cytoplasm and nuclei |

As an example of an Dvl PDZ domain fusion, GST-Dvl PDZ fusion may be prepared from a gene of interest in the following manner. With the full-length gene of interest as the template, the PCR is used to amplify DNA fragments encoding the PDZ domain using primers that introduce convenient restriction endonuclease sites to facilitate sub-cloning. Each amplified fragment is digested with the appropriate restriction enzymes and cloned into a similarly digested plasmid, such as pGEX6P-3 or pGEX-4T-3, that contains GST and is designed such that the sub-cloned fragments will be in-frame with the GST and operably linked to a promoter, resulting in plasmids encoding GST-Dvl PDZ fusion proteins.

To produce the fusion protein, *E. coli* cultures harboring the appropriate expression plasmids are generally grown to mid-log phase ($A_{600}$=1.0) in LB broth, e.g. at about 37° C., and may be induced with IPTG. The bacteria are pelleted by centrifugation, resuspended in PBS and lysed by sonication. The suspension is centrifuged, and GST-Dvl PDZ fusion proteins are purified from the supernatant by affinity chromatography on 0.5 ml of glutathione-Sepharose.

It will be apparent to one of skill in the art that many variations will achieve the goal of isolated Dvl PDZ domain protein and may be used in this invention. For example, fusions of the Dvl PDZ domain and an epitope tag may be constructed as described above and the tags used to affinity purify the Dvl PDZ domain. Dvl PDZ domain proteins/peptides may also be prepared without any fusions; in addition, instead of using the microbial vectors to produce the protein, in vitro chemical synthesis may instead be used. Other cells may be used to produce Dvl PDZ domain proteins/peptides, such as other bacteria, mammalian cells (such as COS), or baculoviral systems. A wide variety of polynucleotide vectors to produce a variety of fusions are also available. The final purification of a Dvl PDZ domain fusion protein will generally depend on the fusion partner; for example, a poly-histidine tag fusion can be purified on nickel columns.

(iii) Determining the Sequence of the Displayed Peptide

Phage(mid) that bind to Dvl PDZ with the desired characteristics (and optionally, does not bind to unrelated sequences), can be subjected to sequence analysis. The phage (mid) particles displaying the candidate binding peptides are amplified in host cells, the DNA isolated, and the appropriate portion of the genome (encoding the candidate peptide) sequenced using any appropriate known sequencing technique.

Other Approaches for Identifying Modulators of Dvl PDZ-Ligand Interaction

Another approach to identify modulators of Dvl PDZ-ligand binding is to incorporate rational drug design; that is, to understand and exploit the biology of the PDZ interaction. In this approach, the critical residues in a PDZ ligand are determined, as is, optionally, the optimal peptide length. Then, small molecules are designed with this information in hand; for example, if a tyrosine is found to be a critical residue for binding to a PDZ domain, then small molecules that contain a tyrosine residue will be prepared and tested as inhibitors. Generally 2,3, 4 or 5 amino acid residues will be determined to be critical for binding and candidate small molecule inhibitors will be prepared containing these residues or the residue sidechains. The test compounds are then screened for their ability to inhibit Dvl PDZ domain-ligand interactions using protocols well-known in the art, for example, a competitive inhibition assay.

Compounds that modulate Dvl PDZ domain-ligand binding interactions are useful to treat diseases and conditions that are associated with dysregulation of binding interactions of Dvl PDZ. Diseases and conditions that are associated with regulation of Dvl PDZ domain interactions include caspase dependent and independent apoptosis, and mitochondria protein quality control.

1. Determining critical residues in an Dvl PDZ binding polypeptide (a) Alanine Scanning Alanine scanning an Dvl PDZ domain binding peptide sequence can be used to determine the relative contribution of each residue in the ligand to PDZ binding. To determine the critical residues in a PDZ ligand, residues are substituted with a single amino acid, typically an alanine residue, and the effect on PDZ domain binding is assessed. See U.S. Pat. No. 5,580,723; U.S. Pat. No. 5,834,250; and the Examples.

(b) Truncations (Deletion Series)

Truncation of an Dvl PDZ domain binding peptide can elucidate not only binding critical residues, but also determine the minimal length of peptide to achieve binding. In some cases, truncation will reveal a ligand that binds more tightly than the native ligand; such a peptide is useful to modulate Dvl PDZ domain:PDZ ligand interactions.

Preferably, a series of Dvl PDZ-domain binding peptide truncations are prepared. One series will truncate the amino terminal amino acids sequentially; in another series, the truncations will begin at the carboxy terminus. As in the case for alanine scanning, the peptides may be synthesized in vitro or prepared by recombinant methods.

(c) Rational Modulator Design

Based on the information obtained from alanine scanning and truncation analysis, the skilled artisan can design and synthesize small molecules, or select small molecule libraries that are enriched in compounds that are likely to modulate binding. For example, based on the information as described in the Examples, a modulator peptide can be designed to include 2 appropriate-spaced hydrophobic moieties.

(d) Binding Assays

Forming a complex of a Dvl PDZ binding peptide and Dvl PDZ facilitates separation of the complexed from the uncomplexed forms thereof and from impurities. Dvl PDZ domain: binding ligand complexes can be formed in solution or where one of the binding partners is bound to an insoluble support. The complex can be separated from a solution, for example using column chromatography, and can be separated while bound to a solid support by filtration, centrifugation, etc. using well-known techniques. Binding the PDZ domain containing polypeptide or the ligand therefor to a solid support facilitates high throughput assays.

Test compounds can be screened for the ability to modulate (e.g., inhibit) the interaction of a binder polypeptide with Dvl PDZ domain in the presence and absence of a candidate binding compound, and screening can be accomplished in any suitable vessel, such as microtiter plates, test tubes, and microcentrifuge tubes. Fusion proteins can also be prepared to facilitate testing or separation, where the fusion protein contains an additional domain that allows one or both of the proteins to be bound to a matrix. For example, GST-PDZ-binding peptide fusion proteins or GST-PDZ domain fusion proteins can be adsorbed onto glutathione sepharose beads (SIGMA Chemical, St. Louis, Mo.) or glutathione derivatized microtiter plates that are then combined with the test compound or the test compound and either the nonadsorbed Dvl PDZ domain protein or PDZ-binding peptide, and the mixture is incubated under conditions allowing complex formation (e.g., at physiological conditions of salt and pH). Following incubation, the beads or microtiter plate wells are washed to remove any unbound components, the matrix immobilized in the case of beads, and the complex determined either directly or indirectly. Alternatively, the complexes can be dissociated from the matrix, and the level of binding or activity determined using standard techniques.

Other fusion polypeptide techniques for immobilizing proteins on matrices can also be used in screening assays. Either a Dvl PDZ binding peptide or Dvl PDZ can be immobilized using biotin-avidin or biotin-streptavidin systems. Biotinylation can be accomplished using many reagents, such as biotin-N-hydroxy-succinimide (NHS; PIERCE Chemicals, Rockford, Ill.), and immobilized in wells of streptavidin coated 96 well plates (PIERCE Chemical). Alternatively, antibodies reactive with Dvl PDZ binding peptides or Dvl PDZ domain but do not interfere with binding of a binding peptide to its target molecule can be derivatized to the wells of the plate, and unbound Dvl PDZ or binder peptide trapped in the wells by antibody conjugation. Methods for detecting such complexes, in addition to those described for the GST-immobilized complexes, include immunodetection of complexes using antibodies reactive with the binder peptides or Dvl PDZ domain.

(e) Assay for Binding: Competition ELISA

To assess the binding affinities of a peptide, proteins or other Dvl PDZ ligands, competition binding assays may be used, where the ability of the ligand to bind Dvl PDZ domain (and the binding affinity, if desired) is assessed and compared to that of a compound known to bind the PDZ domain, for example, a high-affinity binder peptide determined by phage display as described herein.

Many methods are known and can be used to identify the binding affinities of binding molecules (e.g. peptides, proteins, small molecules, etc.); for example, binding affinities can be determined as $IC_{50}$ values using competition ELISAs.

The IC$_{50}$ value is defined as the concentration of binder which blocks 50% of Dvl PDZ domain binding to a ligand. For example, in solid phase assays, assay plates may be prepared by coating microwell plates (preferably treated to efficiently adsorb protein) with neutravidin, avidin or streptavidin. Non-specific binding sites are then blocked through addition of a solution of bovine serum albumin (BSA) or other proteins (for example, nonfat milk) and then washed, preferably with a buffer containing a detergent, such as Tween-20. A biotinylated known Dvl PDZ binder (for example, the phage peptides as fusions with GST or other such molecule to facilitate purification and detection) is prepared and bound to the plate. Serial dilutions of the molecule to be tested with Dvl PDZ domain are prepared and contacted with the bound binder. The plate coated with the immobilized binder is washed before adding each binding reaction to the wells and briefly incubated. After further washing, the binding reactions are detected, often with an antibody recognizing the non-PDZ fusion partner and a labeled (such as horseradish peroxidase (HRP), alkaline phosphatase (AP), or a fluorescent tag such as fluorescein) secondary antibody recognizing the primary antibody. The plates are then developed with the appropriate substrate (depending on the label) and the signal quantified, such as using a spectrophotometric plate reader. The absorption signal may be fit to a binding curve using a least squares fit. Thus the ability of the various molecules to inhibit PDZ domain from binding a known PDZ domain binder can be measured.

Apparent to one of skill are the many variations of the above assay. For example, instead of avidin-biotin based systems, PDZ domain binders may be chemically-linked to a substrate, or simply adsorbed.

2. PDZ Domain Peptide Ligands Found During Phage Display

PDZ domain peptide ligands are potential useful inhibitors of the Dvl PDZ-ligand interaction, including those described in the Examples (and Table I, II, and FIG. 1).

The competitive binding ELISA is a useful means to determine the efficacy of each phage-displayed PDZ-domain binding peptide.

3. Aptamers

Aptamers are short oligonucleotide sequences that can be used to recognize and specifically bind almost any molecule. The systematic evolution of ligands by exponential enrichment (SELEX) process (Ausubel et al., Current protocols in molecular biology. John Wiley & Sons, New York (1987); Ellington and Szostak, *Nature.* 346:818-22 (1990); Tuerk and Gold, *Science.* 249:505-10 (1990)) can be used to find such aptamers. Aptamers have many diagnostic and clinical uses; for almost any use in which an antibody has been used clinically or diagnostically, aptamers too may be used. In addition, aptamers are less expensive to manufacture once they have been identified and can be easily applied in a variety of formats, including administration in pharmaceutical compositions, bioassays and diagnostic tests (Jayasena, *Clin Chem.* 45:1628-50 (1999)).

In the competitive ELISA binding assay described above, the screen for candidate aptamers includes incorporating the aptamers into the assay and determining their ability to modulate Dvl PDZ domain:ligand binding.

4. Antibodies (Abs)

Any antibody that modulates (e.g., inhibits) ligand:Dvl PDZ domain binding can be a modulator (e.g., inhibitor) of Dvl PDZ domain-ligand interaction. Examples of suitable antibodies include polyclonal, monoclonal, single-chain, anti-idiotypic, chimeric Abs, or humanized versions of such antibodies or fragments thereof. Antibodies may be from any suitable source, including of synthetic origin and any species in which an immune response can be raised.

Screening Methods

This invention encompasses methods of screening compounds to identify those that modulate Dvl PDZ-ligand interaction. Screening assays are designed to identify compounds that bind or complex with Dvl PDZ and/or ligand, or otherwise interfere with the interaction of Dvl PDZ and cellular factors. One approach to determining the ability of a candidate compound to be a modulator is to assess the activity of the candidate compound in a competitive inhibition assay in the presence of a known Dvl PDZ binder, such as any of the binder peptides (e.g., the high affinity binders described in the Examples) disclosed herein. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for modulators are common in that they call for contacting the drug candidate with Dvl PDZ (or equivalent thereof) and/or binding ligand that is involved in the binding interaction of Dvl PDZ and the binding ligand, under conditions and for a time sufficient to allow these two components to interact.

In binding assays, the interaction is binding and the complex formed can be isolated or detected in the reaction mixture. In a particular embodiment, a candidate substance or molecule is immobilized on a solid phase, e.g., on a microtiter plate, by covalent or non-covalent attachments. Non-covalent attachment generally is accomplished by coating the solid surface with a solution of the substance/molecule and drying. Alternatively, an immobilized affinity molecule, such as an antibody, e.g., a monoclonal antibody, specific for the substance/molecule to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with, but does not bind to, Dvl PDZ or its binding partner, its interaction with the polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

In any of the screening processes above, it is often desirable to assess the modulatory capability of a candidate compound by determining its binding ability to Dvl PDZ and a known high affinity binder (such as one of those described herein).

Candidate compounds can be generated by combinatorial libraries and/or mutations of known binders based on information described herein, in particular information relating to contributions and importance to Dvl PDZ-ligand binding interactions of individual residues and moieties within a ligand or Dvl PDZ sequence itself.

Compounds that interfere with the interaction of Dvl PDZ and binding ligand can be tested as follows: usually a reaction mixture is prepared containing Dvl PDZ and a ligand under conditions and for a time allowing for the interaction and binding of the two molecules. To test the ability of a candidate compound to inhibit the binding interaction, the reaction is run in the absence and in the presence of the test compound. In addition, a placebo may be added to a third reaction mixture, to serve as positive control. The binding (complex formation) between the test compound and Dvl PDZ and/or binding ligand present in the mixture is monitored, as described hereinabove. The formation of a complex in the control reaction(s) but not in the reaction mixture containing the test compound indicates that the test compound interferes with the interaction of Dvl PDZ and binding ligand.

As described herein, a substance/molecule of the invention can be a peptide. Methods of obtaining such peptides are well known in the art, and include screening peptide libraries for binders to a target antigen. In one embodiment, suitable target antigens would comprise Dvl PDZ (or portion thereof that comprises binding site for a Dvl PDZ ligand), which is described in detail herein. Libraries of peptides are well known in the art, and can also be prepared according to art methods. See, e.g., Clark et al., U.S. Pat. No. 6,121,416. Libraries of peptides fused to a heterologous protein component, such as a phage coat protein, are well known in the art, e.g., as described in Clark et al., supra. In one embodiment, a peptide having ability to block Dvl PDZ protein-protein interaction comprises the amino acid sequence of any of the binder peptides disclosed herein. In another embodiment, a peptide having ability to block Dvl PDZ protein-protein interaction comprises the amino acid sequence of a binder peptide obtained from a modulator screening assay as described above. In one embodiment, the peptide has the ability to compete with one or more of the binder peptides disclosed herein (see Examples) for binding to Dvl PDZ. In one embodiment, the peptide binds to the same epitope on Dvl PDZ to which one or more of the binder peptides disclosed herein (see Examples) bind. Variants of a first peptide binder can be generated by screening mutants of the peptide to obtain the characteristics of interest (e.g., enhancing target binding affinity, enhanced pharmacokinetics, reduced toxicity, improved therapeutic index, etc.). Mutagenesis techniques are well known in the art. Furthermore, scanning mutagenesis techniques (such as those based on alanine scanning) can be especially helpful to assess structural and/or functional importance of individual amino acid residues within a peptide.

Determination of the ability of a candidate substance/molecule of the invention, such as a peptide comprising the amino acid sequence of a binder peptide disclosed herein, to modulate Dvl PDZ activity, can be performed by testing the modulatory capability of the substance/molecule in in vitro or in vivo assays, which are well established in the art, e.g., as described in Martins et al. (*J. Biol. Chem.* 278(49):49417-49427 (2003)) and Faccio et al. (*J. Biol. Chem.* 275(4):2581-2588 (2000)).

Examples of Uses for Dvl PDZ Binders and Modulators of Dvl PDZ-Ligand Interaction The identification and characterization of the Dvl PDZ peptide binders as described herein provide valuable insights into the cellular functions of the Dvl protein, and provides compositions and methods for modulating the in vivo interactions between this important cellular protein and its binding partner(s). For example, these peptides and their homologs can be utilized to interfere with the in vivo binding interactions involving Dvl PDZ. Homologs can be generated conveniently based on their binding and/or functional characteristics relative to the well-characterized peptides provided herein. These peptides can further be utilized to elucidate cellular and physiological polypeptides that constitute Dvl PDZ in vivo complexes.

Well-characterized moderate to high affinity peptide binders of Dvl PDZ as described herein can be further used to elucidate important structural characteristics of Dvl PDZ itself. Knowledge of such provides for development of modulatory agents based on modification of the Dvl PDZ sequence itself. The invention provides Dvl PDZ variants as disclosed herein that have enhanced or reduced ability to bind Dvl PDZ binding partners. Other variants can be similarly identified.

Dvl PDZ-binding partner modulators developed based on the ligand peptides described herein can be used to achieve the modulatory effect of interest. For example, such manipulation may include inhibition of the association between Dvl PDZ domain and its cognate binding protein. In another example, such manipulation may include agonistic effects through, for example, induction of cellular functions as a result of binding of the modulators to Dvl PDZ or through enhancement of association between Dvl PDZ domain and its cognate binding protein by the modulators.

Other uses of modulators of Dvl PDZ include diagnostic assays for diseases related to Dvl and its associating partners, the use of the Dvl PDZ domain and ligands in fusion proteins as purification handles and anchors to substrates.

Identification of binders capable of binding to Dvl PDZ domain at varying affinities, as described herein, provide useful avenues for modulating biologically important protein-protein interactions in vivo. As is well-established in the art, the Dvl protein is implicated in important biological processes, including regulation of apoptosis and protein quality control in mitochondria. The Dvl protein contains a PDZ domain, which is a domain reported to be essential in protein-protein binding interactions. Thus, identification of molecules which are capable of modulating these interactions points to avenues of therapeutic and/or diagnostic applications and strategies that would not be possible in the absence of knowledge of such molecules and interactions. Modulatory compounds (e.g., inhibitory or agonistic) can be delivered into live cells using appropriate routes of administration known in the art, e.g., via microinjection, antenapedia peptide or lipid transfection reagents, to serve as Dvl PDZ domain-specific competitive modulators in order to modulate, and in some instances validate the physiological importance of Dvl PDZ ligand interaction in a particular tissue, cell, organ or pathological condition. Suitable assays exist to monitor the PDZ ligand interaction and the physiological effect of modulation of said interaction. This does not require that the physiological ligand for Dvl PDZ domain is discovered by phage display, only that the modulator is specific for the PDZ domain and of sufficient affinity to disrupt the interaction of said ligand with the PDZ domain. Finally, as with any protein linked with a disease process, one must establish how a drug should affect the protein to achieve therapeutic benefit. Modulatory compounds, such as peptides/ligands, may be delivered into live cells or animal models which are models for a disease (i.e. mimic certain properties of a disease) to determine if disruption of Dvl PDZ-ligand interaction by the modulatory compound of interest provides an outcome consistent with expectations for therapeutic benefit.

Methods of detecting protein-protein (or peptide) interactions in vivo are known in the art. For example, the methods described by Michnick et al. in U.S. Pat. Nos. 6,270,964 B1 & 6,294,330 B1 can be used to analyze interactions of Dvl PDZ domain-containing protein (including any described herein) and a cognate ligand or synthetic peptide (including any described herein). Furthermore, these methods can be used to assess the ability of a molecule, such as a synthetic peptide, to modulate the binding interaction of Dvl PDZ-domain protein and its cognate ligand in vivo.

Therapeutic/Prophylactic Applications

Compounds that have the property of increasing or decreasing Dvl PDZ protein activity are useful. This increase in activity may come about in a variety of ways, for example by administering to a subject in need thereof an effective amount of one or more of the modulators described herein.

"Antagonists" or "negative modulators" include any molecule that partially or fully blocks, inhibits, or neutralizes a biological activity of Dvl PDZ and/or its endogenous ligand(s). Similarly, "agonists" or "positive modulators" include any molecule that mimics or enhances a biological activity of Dvl PDZ and/or its endogenous ligand(s). Molecules that can act as agonists or antagonists include the modulators of Dvl PDZ-binder/ligand interaction described herein, including but not limited to Abs or antibody fragments, fragments or variants of Dvl PDZ/ligands/binders, peptides, small organic molecules, etc.

The invention provides various methods based on the discovery of various binding molecules capable of interacting specifically with Dvl PDZ, and the identification of unique characteristics of the binding interactions between Dvl PDZ and ligand binding peptides.

Various substances or molecules (including peptides, etc.) may be employed as therapeutic agents. These substances or molecules can be formulated according to known methods to prepare pharmaceutically useful compositions, whereby the product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a substance or molecule of the invention is employed, normal dosage amounts may vary from about 10 ng/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a substance or molecule is desired in a formulation with release characteristics suitable for the treatment of any disease or disorder requiring administration of the substance or molecule, microencapsulation of the substance or molecule is contemplated. Microencapsulation of recombinant proteins for sustained release has been successfully performed with human growth hormone (rhGH), interferon-(rhIFN-), interleukin-2, and MN rgp120. Johnson et al., *Nat. Med.*, 2:795-799 (1996); Yasuda, *Biomed. Ther.*, 27:1221-1223 (1993); Hora et al., *Bio/Technology*, 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

Pharmaceutical Compositions

A modulator molecule/substance of the invention can be incorporated into compositions, which in some embodiments are suitable for pharmaceutical use. Such compositions typically comprise the nucleic acid molecule, peptide/protein, small molecule and/or antibody, and an acceptable carrier, for example one that is pharmaceutically acceptable. A "pharmaceutically acceptable carrier" includes any and all solvents, dispersion media, coatings, antibacterial and antifungal agents, isotonic and absorption delaying agents, and the like, compatible with pharmaceutical administration (Gennaro, Remington: The science and practice of pharmacy. Lippincott, Williams & Wilkins, Philadelphia, Pa. (2000)). Examples of such carriers or diluents include, but are not limited to, water, saline, Finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

1. General Considerations

A pharmaceutical composition is formulated to be compatible with its intended route of administration, including intravenous, intradermal, subcutaneous, oral (e.g., inhalation), transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

2. Injectable Formulations

Pharmaceutical compositions suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents; for example, parabens, chlorobutanol, phenol, ascorbic acid, and thimerosal, can contain microorganism contamination. Isotonic agents; for example, sugars, polyalcohols such as manitol, sorbitol, and sodium chloride can be included in the composition. Compositions that can delay absorption include agents such as aluminum monostearate and gelatin.

Sterile injectable solutions can be prepared by incorporating the active compound (e.g., any modulator substance/molecule of the invention) in the required amount in an appropriate solvent with one or a combination of ingredients as required, followed by sterilization. Generally, dispersions are prepared by incorporating the active compound into a sterile vehicle that contains a basic dispersion medium, and the other required ingredients. Sterile powders for the preparation of sterile injectable solutions, methods of preparation include vacuum drying and freeze-drying that yield a powder containing the active ingredient and any desired ingredient from a sterile solutions.

3. Oral Compositions

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

4. Compositions for Inhalation

For administration by inhalation, the compounds are delivered as an aerosol spray from a nebulizer or a pressurized container that contains a suitable propellant, e.g., a gas such as carbon dioxide.

5. Systemic Administration

Systemic administration can also be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams.

The compounds can also be prepared in the form of suppositories (e.g., with bases such as cocoa butter and other glycerides) or retention enemas for rectal delivery.

6. Carriers

In one embodiment, the active compounds are prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art. Liposomal suspensions can also be used as pharmaceutically acceptable carriers. These can be prepared according to methods known to those skilled in the art, such as in (Eppstein et al., U.S. Pat. No. 4,522,811, 1985).

7. Unit Dosage

Oral formulations or parenteral compositions in unit dosage form can be created to facilitate administration and dosage uniformity. Unit dosage form refers to physically discrete units suited as single dosages for the subject to be treated, containing a therapeutically effective quantity of active compound in association with the required pharmaceutical carrier. The specification for the unit dosage forms are dictated by, and directly dependent on, the unique characteristics of the active compound and the particular desired therapeutic effect, and the inherent limitations of compounding the active compound.

8. Gene Therapy Compositions

The nucleic acid molecules can be inserted into vectors and used as gene therapy vectors. Gene therapy vectors can be delivered to a subject by, for example, intravenous injection, local administration (Nabel and Nabel, U.S. Pat. No. 5,328,470, 1994), or by stereotactic injection (Chen et al., *Proc Natl Acad Sci USA*. 91; 3054-7 (1994)). The pharmaceutical preparation of a gene therapy vector can include an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

9. Dosage

The pharmaceutical composition and method may further comprise other therapeutically active compounds that are usually applied in the treatment of Dvl protein-related (specifically Dvl PDZ-related) conditions.

In the treatment or prevention of conditions which require Dvl PDZ-ligand modulation, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

However, the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

10. Kits for Compositions

The compositions (e.g., pharmaceutical compositions) can be included in a kit, container, pack, or dispenser together with instructions for administration. When supplied as a kit, the different components of the composition may be packaged in separate containers and admixed immediately before use. Such packaging of the components separately may permit long-term storage without losing the active components' functions.

Kits may also include reagents in separate containers that facilitate the execution of a specific test, such as diagnostic tests or tissue typing.

(a) Containers or vessels

The reagents included in kits can be supplied in containers of any sort such that the life of the different components are preserved and are not adsorbed or altered by the materials of the container. For example, sealed glass ampules may contain lyophilized modulator substance/molecule and/or buffer that have been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

(b) Instructional materials

Kits may also be supplied with instructional materials. Instructions may be printed on paper or other substrate, and/or may be supplied as an electronic-readable medium, such as a floppy disc, CD-ROM, DVD-ROM, Zip disc, videotape, laserdisc, audio tape, etc. Detailed instructions may not be physically associated with the kit; instead, a user may be directed to an Internet web site specified by the manufacturer or distributor of the kit, or supplied as electronic mail.

The following examples are included to demonstrate preferred embodiments of the present invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing form the spirit and scope of the invention.

EXAMPLES

Material and Methods

Materials—Enzymes and M13-KO7 helper phage were from New England Biolabs (Ipswich, Mass.). Maxisorp immunoplates plates were from Nalgen NUNC International (Naperville, Ill.). *Escherichia coli* (*E. coli*) XL1-Blue and *E. coli* BL21(DE3) were from Stratagene (La Jolla, Calif.). Plasmid pGEX, horseradish peroxidase/anti-GST antibody conjugate, glutathione Sapharose-4B, and Superdex-75 were from Amersham Pharmacia Biotech (Piscataway, N.J.). 3,3', 5,5'-Tetramethyl-benzidine/$H_2O_2$ (TMB) peroxidase substrate was from Kirkegaard and Perry Laboratories, Inc. (Gaithersburg, Md.). NeutrAvidin was from Pierce Biotechnology, Inc. (Rockford, Ill.). Anti-Dvl1,2,3 were purchased from Santa Cruz Biotechnology (Santa Cruz, Calif.). Polyclonal anti-β-catenin was from Genentech, Inc. (South San Francisco, Calif.). HEK293S and human non-small cell lung cancer cell line H1703 was from American Type Culture Collection (Manassas, Va.). FuGene 6 was from Roche Molecular Biochemicals (Mannheim, Germany). Lipofectamine was from Invitrogen (Carlsbad, Calif.). Alamar Blue™ was from Pierce Biotechnology, Inc. (Rockford, Ill.).

Oligonucleotides—Equimolar DNA degeneracies were represented in the TUB code (K=G/T, N=A/C/G/T, V=A/C/G, W=A/T). Degenerate codons are shown in bold text. The following oligonucleotides were used for the construction of phage-displayed peptide libraries:

```
X10a:
                                                (SEQ ID NO: 181)
ACATCGACAGCGCCCCCGGTGGC
GGA(NNK)10TGATAAACCGATACA
```

Synthetic Peptides—Peptides were synthesized using standard 9-fluorenylmethoxycarbonyl (Fmoc) protocols, cleaved off the resin with 2.5% triisopropylsilane and 2.5% $H_2O$ in trifluoroacetic acid, and purified by reversed-phase high performance liquid chromatography. The purity and mass of each peptide were verified by liquid chromatography/mass spectrometry.

Library Construction and Sorting—Peptide libraries were displayed as fusions to the C terminus of a mutant M13 major coat protein designed for high valency display[10] as described. The N-terminal library was constructed as previously described[11]. Each library contained $2\times10^{10}$ unique members.

The libraries were cycled through rounds of binding selection with a GST-Dvl2PDZ fusion protein coated on 96-well Maxisorp immunoplates as the capture target. Phage were propagated in *E. coli* XL1-blue with M13-KO7 helper phage and 10 μM IPTG. After four rounds of binding selection, individual phage clones were analyzed in a high-throughput phage ELISA, and positive clones were subjected to DNA sequence analysis.

Protein Purification—GST-Dvl2PDZ fusion proteins were produced and purified using the pGEX *E. coli* expression system, as recommended by the manufacturer. For Dvl2PDZ domain, protein fragments spanning amino acids 248-364 of the full-length Dvl2 were produced.

Affinity assays—The binding affinities of peptides for Dvl2PDZ were determined as $IC_{50}$ values using a competition ELISA, as previously described[12]. The $IC_{50}$ value was defined as the concentration of peptide that blocked 50% of PDZ domain binding to immobilized peptide. Assay plates were prepared by immobilizing an amino-terminally biotinylated peptide (KWYGWL$_{—COOH}$) (SEQ ID NO: 169) on Maxisorp immunoplates coated with neutravidin and blocked with BSA. A fixed concentration of GST-PDZ fusion protein (600 nM) in PBS, 0.5% BSA, 0.1% Tween 20 (PBT buffer) was preincubated for 1 h with serial dilutions of peptide and then transferred to the assay plates. After 15 min incubation, the plates were washed with PBS, 0.05% Tween 20, incubated with a mixture of anti-GST antibody (0.5 μg/ml) and horseradish peroxidase/rabbit anti-mouse IgG antibody conjugate (1:2000 dilution) in PBT buffer, washed again, and detected with TMB peroxidase substrate.

The binding affinities of synthetic peptides were also measured by Flourescence polarization assay. Serial dilution of purified Dvl2PDZ domain polypeptide (1-10 μM) was incubated with 10 nM probe peptide (FAM-KWYGWL-COOH) (SEQ ID NO: 169) in PBS, 0.1% Triton X100 as 30 μl volume in 96-well black HE96 plates (LJL Biosystem, Inc, Calif.), and incubated for 15 minutes at room temperature. Polarization measurements were performed in Analyst platereader (LJL Biosystems, Inc., Sunnyvale, Calif.). $K_s$=536 nM was derived from this assay by non-linear regression fitting with KaleidaGraph™. Competition experiments were performed by addition of serial dilution of the free peptides (0-500 μM) to solution with 10 nM probe and 1 μM Dvl2PDZ. The polarization was measured and IC50 values were derived as described above. $K_i$ values were calculated as described previously [15].

Pull-down Assays—GST or GST-DVLpep fusion protein (GST fused with peptide GGGKWYGWL (SEQ ID NO: 182) at its C-terminus) was bound to glutathione Sepharose-4B following standard protocols, and bound proteins were quantified by SDS-PAGE using known amounts of BSA as standards. Beads carrying protein (2-10 μg) were incubated with cell extract of HEK293S cell overnight at 4° C. The cell extracts were prepared by lysing the cell in SJC lysis buffer. The whole protein concentration was determined by BCA protein kit (Promega; Madison, Wis.) and normalized to 1 mg/ml. The beads were washed with washing buffer (PBS, 0.5% BSA, 0.1% Tween 20) for 10 times and resuspended in SDS sample buffer, incubated at 90° C. for 10 min and the supernatant was subjected to SDS-PAGE. Bound proteins were blotted by anti-Dvl1, anti-Dvl2 and anti-Dvl3 and analyzed by Li-core™.

Cell culture, transfection and peptide treatment: HEK293 and H1703 were propagated according to the instructions from American Type Culture Collection. HEK293 cells were transfected with FuGene6 according to the manufacturer's instructions (Roche Molecular Biochemicals) at cell confluence of 50%. H1703 cells were transfected with Lipofectamine according to manufacturer's instruction at cell confluence of 80%. Cells were treated with medium containing peptide (5 μM-40 μM) 24 hours after transfection, and were routinely harvested 24 hours after the peptide treatment for additional assays.

TOPGLOW assay: Cells were plated in 12-well plates. The TOPGLOW reporter plasmid was transfected transiently into cells as described above. TCF-mediated gene transcription was determined by pTOPGLOW luciferase activity, which was normalized to relative luciferase activities of pRL reporter (cotransfected internal control). All experiments were performed duplicated.

Western Blot: Harvested cells were lysed with SIC lysis buffer, the supernatant was subjected to SDS-PAGE, which was transferred, blocked and blotted with proper primary antibody by a standard western blot protocol. Fluorescence labeled secondary antibodies (Alexa goat anti-mouse or anti-rabbit) were added and the results were analyzed by Li-core™.

Cell viability assay: Cells were seeded in black wall 96-well plate in triplicate and treated with various doses of peptide on Day 0 and were incubated at 37° C. in a humid incubator with 5% $CO_2$. After 72 hours, Alamar Blue assay was performed according to the instruction from manufacturer. For cell growth profile, the cells were seeded in black wall 96-well plate in triplicate and treated with 10 μM peptide or DMSO on Day 0, and cell viability was measured by Alamar Blue assay after 24, 48 and 72 hours.

Results

Peptides selected for binding to Dvl2PDZ—Phage-displayed peptide libraries were used to select ligands that bound to Dvl2PDZ, as described previously[12]. We used decapeptide libraries fused to the C-terminus or N-terminus of the phage coat protein. The library contained NNK degenerate codons that encoded all 20 natural amino acids. The possible occurrence of amber stop codons in the degenerate codon also provided for the display of shorter peptides for the C-terminal library. Each library was cycled through four rounds of binding selection with immobilized GST-Dvl2PDZ fusion protein as the capture target.

The sequencing of 90 clones from the C-terminal library revealed a unique binding motif (FIG. 1A). The binding motif contains a highly conserved Gly at −2 position, Trp/Tyr at −1 position, Phe/Leu at 0 position and a hydrophobic or aromatic residue at −3 position, which is different from any known canonical PDZ binding motif. Interestingly, this binding motif is conserved in orthologous disheveled protein in *C. elegans*. (data not shown).

The sequencing of 127 clones from the N-terminal library revealed 4 types of internal binding motifs (FIG. 1B). Motifs type I and type II are similar to those derived from the C-terminal library. For ease of reference herein, we designated the same position numbering system to the consensus sequence, that is, the core sequence for both Type I and II is $Tyr^{-3}Gly^{-2}Trp^{-1}[Ile/Val]^0$ (FIG. 1B). The two motif types differ at the residue that follows position 0. For type I, a tri-glycine linker sequence invariably follows Ile/Val0, whereas type II has a highly conserved Asp at position 1 followed by a tri-glycine linker In addition, type I has a slightly greater preference for Asp at position −4 than type II.

Motifs type III and type IV represent entirely different binding patterns. These two types share a core WXDXP motif, with major differences at X as well as flanking positions. Using the same position numbering system as above discussed, we designate the core positions as $Trp^{-1}X^0Asp^1X^2P^3$. Motif type III prefers Ser/Thr at position 0, Ile/Phe/Leu at position 2, Leu at position −2 and mostly Leu/Val at position −3; whereas motif type IV prefers Ile/Val at position 0, Gly at position 2, promiscuous (a variety of amino acids) at position −2 and mostly Glu at position −3. The highly conserved Pro at position 3 for both types indicates a structured peptide is required for such kind of interaction between the ligand and Dvl PDZ domain. Trp is conserved in all types of Dvl PDZ ligands, suggesting its role as the anchoring point for ligand binding. The highly conserved $Asp^1$ may mimic the canonical interaction between PDZ domains with a free carboxyl group. The differences of position −3, −2, 0 and/or 2 between motif type III and motif type IV suggest that the coordination of these positions is associated with the different specificity of the ligands.

Affinity assays with synthetic peptides-Peptides corresponding to the dominant selected sequence ($KWYGWL_{COOH}$ (D1)) (SEQ ID NO: 169) and its derivatives with single mutation, as well as N-terminal extension (D2-4) were synthesized and assayed for binding to Dvl2PDZ (Table I). Peptide D1 bound with high affinity ($IC_{50}$=1.3 μM), while a peptide with substitution of Leu with Phe at the 0 position (D2) bound with approximately similar affinity ($IC_{50}$=0.93 μM). It was also found that a hydrophobic or aromatic residue, especially a Trp, in upstream positions of the ligand could enhance the binding affinity significantly, as seen with peptides with a Trp extension at −6 position (D3 and D4). The binding affinities of these peptides were enhanced up to 10 fold. Wong et. al. have reported that the binding affinity between a Frizzled internal peptide ligand and DvlPDZ to be 9.5 μM, and that such interaction plays important role in Wnt signal transduction[3]. Our phage-derived DvlPDZ peptide ligands binds to DvlPDZ with up to 100-fold higher affinity compared to native interactions, and therefore are potential antagonists for the Wnt signaling pathway.

TABLE I $IC_{50}$ values for synthetic peptides binding to Dvl2PDZ (SEQ ID NOS 169, 177-179 and 183, respectively, in order of appearance). The $IC_{50}$ values are the mean concentrations of peptide that blocked 50% of Dvl2PDZ binding to an immobilized high affinity peptide ligand in a competition ELISA. The N-termini of peptides in the series were acetylated.

| Peptide ID | sequence | IC50 (uM) |
|---|---|---|
| D1 | K W Y G W L | 1.34 ± 0.21 |
| D2 | K W Y G W F | 0.93 ± 0.20 |
| D3 | W K W Y G W L | 0.14 ± 0.01 |
| D4 | W K W Y G W F | 0.31 ± 0.06 |
| D5 | K G F G M L | 242.9 ± 73.8 |

Through a database search with consensus motif of [YLFI]G[WMFY][FL]$_{COOH}$, we identified a potential natural ligand for Dvl, a human ubiquitin protein ligase E3A (UBE3A), which contains C-terminal sequence of YAKGFGML$_{COOH}$ [13] (SEQ ID NO: 170). Hexapeptide corresponding to this sequence (KGFGML$_{COOH}$) (SEQ ID NO: 183) was synthesized (D5) and assayed for affinity. It bound to Dvl2PDZ with a much weaker affinity ($IC_{50}$=242 μM) compared to D1 or D2, indicating that Trp at −1 position is energetically important for tight binding. Nonetheless, since protein-ligand interaction even at 200 μM has been thought to be biologically relevant based on previous studies on MagiPDZ2-PTPN interaction[14], the weak interaction between UBE3A and Dvl is therefore possible.

Flourescence polarization assay was used to measure the affinity of two internal peptide ligands N2 and N3 to DvlPDZ domain. See Table II. The $K_i$ value for D1 measured by this method is 725 nM, which is consistent with the IC50 value measured by competition ELISA (Table I). Since the motifs of N2 and D1 are quite similar, it was expected that the affinity of N2 to DvlPDZ would be similar to that of D1 ($K_i$=1.2 μM), whereas N3 has a distinct binding motif from D1 and N2, and the affinity of N3 ($K_i$=4.6 μM) was 6-fold lower than that of D1, indicating a distinct binding pattern between DvlPDZ domain and N3 ligand from that of D1 or N2.

TABLE II $K_i$ values measured by Flourescence polarization assay for synthetic peptides binding to Dvl2PDZ (SEQ ID NOS: 169, 180 and 171, respectively, in order of appearance). The $K_i$ values were measured and calculated as described in Materials and Methods. The N-termini of peptides in the series were acetylated. The C-termini of N2 and N3 were amidated

| peptide ID | Sequence | Ki (nM) |
|---|---|---|
| D1 | K W Y G W L | 725.1 |
| N2 | G W K D Y G W I D G | 1211.1 |
| N3 | G E I V L W S D I P G | 4618.9 |

DvlPDZ peptide ligand interacts with all 3 endogenous Dvl: There are 3 genes in human coding for three Disheveled proteins (Dvl1, Dvl2 and Dvl3). The overall homologies among these proteins are ~60%. In particular, the PDZ domains of the three Dvl protein are highly homologous to each other (>85%) (FIG. 2A). Therefore, although peptide D1 is the phage-derived ligand to Dvl2PDZ, we believed that it was likely to bind to the other two Dvl PDZ domains as well. To confirm that D1 could bind to all three endogenous Dvl proteins in vivo, a GST fusion construct in which the C-terminus of GST was fused with D1 sequence linked with 3 Gly (GST-Dvlpep) was constructed and conjugated to glutathione Sepharose-4B. Cell lysate of HEK293 was pulled down by either GST alone or GST-Dvlpep conjugated beads. All three endogenous Dvl could be detected in crude cell lysate of HEK293, and could be pulled down by GST-Dvlpep as expected (FIG. 2B).

Inhibition of the canonical Wnt pathway by DvlPDZ peptide ligand: To investigate the effects of DvlPDZ peptide ligands on cells that are responsive to Wnt signaling, we synthesized cell-penetrating peptide ligands for DvlPDZ having the following sequences:

```
                                        (SEQ ID NO: 173)
(i)     Ac-RQIKIWFQNRRMKWKKKWYGWL (DVLp_C), (SEQ ID NO: 174)
(ii)    Ac-RQIKIWFQNRRMKWKKGWKDYGWIDG (DVLp_N2), (SEQ ID NO: 175)
(iii)   Ac-RQTKIVWFQNRRMKKGEIVLWSDIPG (DVLp_N3), (SEQ ID NO: 176)
(iv)    Ac-RQIKIWFQNRRMKWKKGSGNEVWIDGPG (DVLp_N4);
and (SEQ ID NO: 172)
(v)     Ac-RQTKIWFQNRRMKWKK (PEN)--a negative
        control peptide with cell-penetrating
        sequence alone.
```

We tested the effects using the standard TopGlow assay. HEK293 cells were transfected with TopGlow gene and the cells were treated with different doses of peptides DVLp_C, DVLp_N2, DVLp_N3, DVLA N4 or PEN (5-20 μM in medium) 24 hours after transfection. At concentrations up to 20 μM, two out of four DvlPDZ peptide ligands, DVLp_C and DVLp_N3, inhibited Wnt3a-stimulated transcriptional activity significantly (FIG. 3A) and the inhibition effects were in a dose-dependent manner (FIGS. 3B and 3C). Particularly, DVLp_N3 could inhibit up to 80% of Wnt3a-stimulated transcriptional activity, whereas DVLp_C achieved about 50% inhibition. PEN treated cells did not show an inhibition effect. See FIG. 3. We also compared the β-catenin level in whole cell lysate with treatments of DMSO, DVLp_C, DVLp_N3 or PEN, and found that DVLp_C and DVLp_N3-treated cells had significantly lower β-catenin levels compared to that of both DMSO and PEN-treated cells upon Wnt3a stimulation. See FIGS. 3D and 3E. The inhibition of Wnt-stimulated β-catenin signaling and the reduction of the Wnt-stimulated increase in β-catenin protein level caused by treatment with DvlPDZ ligand peptides suggested that DvlPDZ domain is engaged in an interaction that is involved in canonical Wnt/β-catenin signal pathway, which can be antagonized by, for example, DvlPDZ peptide ligands DVLp_C and DVLp_N3.

Peptide ligand of DvlPDZ can suppress cancer cell growth: Overexpression of Dvl3 in (6 out of 8) non-small cell lung cancer (NSCLC) tumor samples has been reported [7]. Suppression of Dvl3 with siRNA was shown to block Wnt-stimulated β-catenin signaling and suppress the growth of the NSCLC cell line NCI-H1703 [7]. To assess the effect of DvlPDZ peptide ligand on an NSCLC cell line, NCI-H1703 was treated with DVLp_C, and Wnt-stimulated β-catenin signaling was measured by TopGlow assay. Similar to HEK293S cells, Tcf-stimulated transcriptional activity of NCI-H1703 was inhibited by DVLp_C treatment significantly (FIG. 4). To test the effect of DvlPDZ peptide ligand on NSCLC cell growth, we treated NCI-H1703 with DVLp_C or PEN at doses of 0, 2.5 μM, 5 μM, 10 μM and 20 μM on day 0, incubated for 72 hours, and assayed cell viability with Alamar blue as described above. Without Wnt3a stimulation, DVLp_C-treated cells showed much lower viability than PEN-treated cells at a peptide dose over 10 μM; with Wnt3a stimulation, the lower viability of DVLp_C-treated cells compared to PEN-treated cells could be observed at a peptide dose of 5 μM (FIG. 5A). In addition, as indicated in FIG. 5B, the cell growth profile of DVLp_C-treated NCI-H1703 was much slower than that of DMSO or PEN-treated cells. These results indicated the high-affinity DvlPDZ peptide ligands described herein could effectively suppress growth of tumor cells, such as NSCLC cells.

CONCLUSION

Phage-derived DvlPDZ peptide ligands exhibit high binding affinity to Dvl2PDZ in vitro, with affinities approximately 100-fold higher than the reported binding affinity between Dvl PDZ domain and its natural ligand, the internal sequence at the C-terminal region of Frizzled [3]. Data reported herein show that two cell penetrating DvlPDZ peptide ligands (DVLp_C and DVLp_N3) blocked the Wnt-stimulated β-catenin signaling in HEK293S and one (DVLp_C) also in NCI-H1703, likely through a Dvl PDZ domain-mediated interaction. In particular, the blockage of Wnt-stimulated β-catenin signaling of NCI-H1703, a non-small cell lung cancer cell line, by DvlPDZ peptide ligand DVLp_C effectively suppressed the cell growth. The phage-derived DvlPDZ peptide ligands described herein are potential small molecule leads for cancer treatment, and further can be used to identify additional Dvl PDZ modulators for use as diagnostics and therapeutics.

PARTIAL LIST OF REFERENCES

1. Polakis, P., *Wnt signaling and cancer*. Genes Dev, 2000. 14(15): p. 1837-51.
2. Wharton, K. A., Jr., *Runnin' with the Dvl: proteins that associate with Dsh/Dvl and their significance to Wnt signal transduction*. Dev Biol, 2003. 253(1): p. 1-17.
3. Wong, H. C., et al., *Direct binding of the PDZ domain of Dishevelled to a conserved internal sequence in the C-terminal region of Frizzled*. Mol Cell, 2003. 12(5): p. 1251-60.
4. Oshita, A., et al., *Identification and characterization of a novel Dvl-binding protein that suppresses Wnt signalling pathway*. Genes Cells, 2003. 8(12): p. 1005-17.
5. Cheyette, B. N., et al., *Dapper, a Dishevelled-associated antagonist of beta-catenin and JNK signaling, is required for notochord formation*. Dev Cell, 2002. 2(4): p. 449-61.
6. Zhang, L., et al., *Dapper 1 antagonizes Wnt signaling by promoting dishevelled degradation*. J Biol Chem, 2006.
7. Uematsu, K., et al., *Activation of the Wnt pathway in non small cell lung cancer: evidence of dishevelled overexpression*. Oncogene, 2003. 22(46): p. 7218-21.
8. Uematsu, K., et al., *Wnt pathway activation in mesothelioma: evidence of Dishevelled overexpression and transcriptional activity of beta-catenin*. Cancer Res, 2003. 63(15): p. 4547-51.
9. Shan, J., et al., *Identification of a specific inhibitor of the dishevelled PDZ domain*. Biochemistry, 2005. 44(47): p. 15495-503.

10. Held, H. A. and S. S. Sidhu, *Comprehensive mutational analysis of the M13 major coat protein: improved scaffolds for C-terminal phage display.* J Mol Biol, 2004. 340(3): p. 587-97.

11. Sidhu, S. S. et al., *Phage display for selection of novel binding peptides.* Methods Enzymol., 2000. 328: p. 333-63.

12. Laura, R. P., et al., *The Erbin PDZ domain binds with high affinity and specificity to the carboxyl termini of delta-catenin and ARVCF.* J Biol Chem, 2002. 277(15): p. 12906-14.

13. Huang, L., et al., *Structure of an E6AP-UbcH7 complex: insights into ubiquitination by the E2-E3 enzyme cascade.* Science, 1999. 286(5443): p. 1321-6.

14. Fuh, G., et al., *Analysis of PDZ domain-ligand interactions using carboxyl-terminal phage display.* J Biol Chem, 2000. 275(28): p. 21486-91.

15. Keating, S., et al., *Putting the pieces together: Contribution of fluorescence polarization assays to small molecule lead optimization.* Proceedings of SPIE, 2000. 3913: p. 128-137.

---

The invention claimed is:

1. An isolated polypeptide that binds specifically to Dvl PDZ, wherein the polypeptide comprises the amino acid sequence X1-X2-W—X3-D-X4-P (SEQ ID NO: 186), and wherein X1 is L or V, X2 is L, X3 is S or T, and X4 is I, F or L.

2. The polypeptide of claim 1, wherein the polypeptide comprises the amino acid sequence GEIVLWSDIPG (SEQ ID NO: 171).

3. An isolated polypeptide consisting of the amino acid sequence GEIVLWSDIPG (SEQ ID NO: 171).

4. The polypeptide of any one of claims 1, 2, or 3, wherein the polypeptide inhibits endogenous Dvl-mediated Wnt signaling.

5. A composition comprising the polypeptide of any one of claims 1, 2, or 3.

6. A composition comprising the polypeptide of claim 3.

7. The polypeptide of any one of claims 1, 2, or 3, wherein the polypeptide is linked to an amino acid sequence tag that enhances polypeptide cell entry.

8. A composition comprising the polypeptide of claim 7.

9. The polypeptide of claim 7, wherein the polypeptide inhibits endogenous Dvl-mediated Wnt signaling.

10. The polypeptide of claim 7, wherein the amino acid sequence tag comprises the amino acid sequence of SEQ ID NO: 172.

11. A composition comprising the polypeptide of claim 10.

12. The polypeptide of claim 10, wherein the polypeptide inhibits endogenous Dvl-mediated Wnt signaling.

13. A polypeptide essentially of the amino acid sequence of SEQ ID NO: 176.

14. A composition comprising the polypeptide of claim 13.

15. A method of identifying a compound capable of modulating Dvl PDZ-ligand interaction, said method comprising contacting a sample comprising:
(i) Dvl PDZ,
(ii) one or more of the polypeptides of claim 1;
with
a candidate compound;
and determining the amount of Dvl PDZ-ligand interaction in the presence of the candidate compound;
whereby a change in the amount of Dvl PDZ-ligand interaction in the presence of the candidate compound compared to the amount in the absence of the compound indicates that the candidate compound is a compound capable of modulating Dvl PDZ-ligand interaction.

* * * * *